(12) United States Patent
Basilion et al.

(10) Patent No.: US 10,363,309 B2
(45) Date of Patent: Jul. 30, 2019

(54) TARGETED NANOPARTICLE CONJUGATES

(75) Inventors: James Basilion, Shaker Heights, OH (US); Clemens Burda, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 13/983,750

(22) PCT Filed: Feb. 5, 2012

(86) PCT No.: PCT/US2012/023985
§ 371 (c)(1),
(2), (4) Date: Oct. 2, 2013

(87) PCT Pub. No.: WO2012/106713
PCT Pub. Date: Aug. 9, 2012

(65) Prior Publication Data
US 2014/0044791 A1 Feb. 13, 2014

Related U.S. Application Data

(60) Provisional application No. 61/439,443, filed on Feb. 4, 2011.

(51) Int. Cl.
*A61K 41/00* (2006.01)
*A61K 47/69* (2017.01)

(52) U.S. Cl.
CPC ...... *A61K 41/0071* (2013.01); *A61K 47/6923* (2017.08); *A61K 47/6935* (2017.08)

(58) Field of Classification Search
CPC ............ A61K 41/0071; A61K 47/6923; A61K 47/6935
See application file for complete search history.

(56) References Cited

U.S. PATENT DOCUMENTS

| | | |
|---|---|---|
| 2006/0222595 A1 | 10/2006 | Mukherjee et al. |
| 2008/0213377 A1 | 9/2008 | Bhatia et al. |
| 2009/0011004 A1 | 1/2009 | Lutz et al. |
| 2009/0297615 A1 | 12/2009 | Wang et al. |
| 2009/0304803 A1* | 12/2009 | Hasan ............................ 424/497 |
| 2010/0183504 A1* | 7/2010 | Chen ............................ 424/1.29 |
| 2011/0262347 A1* | 10/2011 | Ruoslahti et al. ............ 424/1.11 |
| 2012/0282632 A1* | 11/2012 | Chiu et al. .................... 435/7.23 |
| 2013/0289520 A1* | 10/2013 | Febvay et al. ................. 604/501 |
| 2013/0315834 A1* | 11/2013 | Praveen et al. ................ 424/9.6 |
| 2014/0220143 A1* | 8/2014 | Dhar et al. .................... 424/490 |

OTHER PUBLICATIONS

Choi et al. Mechanism of active targeting in solid tumors with transferrin-containing gold nanoparticles. Proc Natl Acad Sci U S A. Jan. 19, 2010;107(3):1235-1240.*
Li et al. Identification and characterization of a novel peptide ligand of epidermal growth factor receptor for targeted delivery of therapeutics. FASEB J. Dec. 2005;19(14):1978-1985.*
Otsuka et al. PEGylated nanoparticles for biological and pharmaceutical applications. Advanced Drug Delivery Reviews vol. 55, Issue 3, Feb. 24, 2003, pp. 403-419.*
Samia et al. Semiconductor Quantum Dots for Photodynamic Therapy. J. Am. Chem. Soc. 2003, 125:15736.*
Cheng et al. Highly Efficient Drug Delivery with Gold Nanoparticle Vectors for in Vivo Photodynamic Therapy of Cancer. J. Am. Chem. Soc. 2008, 130, 10643-10647.*
Choi et al. Mechanism of active targeting in solid tumors with transferrin-containing gold nanoparticles. PNAS 2010 107(3):1235-1240.*
Li et al. Identification and characterization of a novel peptide ligand of epidermal growth factor receptor for targeted delivery of therapeutics. The FASEB J. 2005 19(14):1978-1984.*
Ikuta et al. The effect of molecular structure on the anticancer drug release rate from prodrug nanoparticles. Chem. Commun., 2015, 51, 12835-12838.*
Steichen et al. A review of current nanoparticle and targeting moieties for the delivery of cancer therapeutics. Eur J Pharm Sci. Feb. 14, 2013; 48(3): 416-427.*

* cited by examiner

*Primary Examiner* — Robert A Wax
*Assistant Examiner* — Olga V Tcherkasskaya
(74) *Attorney, Agent, or Firm* — Tarolli, Sundheim, Covell & Tummino LLP

(57) ABSTRACT

A composition for treating a disorder in a subject includes a polyethylene glycolylated (PEGylated) nanoparticle, at least one hydrophobic therapeutic agent coupled to the surface of the nanoparticle; and at least one targeting moiety coupled to polyethylene glycol of the nanoparticle for targeting the composition to a cell associated with disorder.

16 Claims, 18 Drawing Sheets
Specification includes a Sequence Listing.

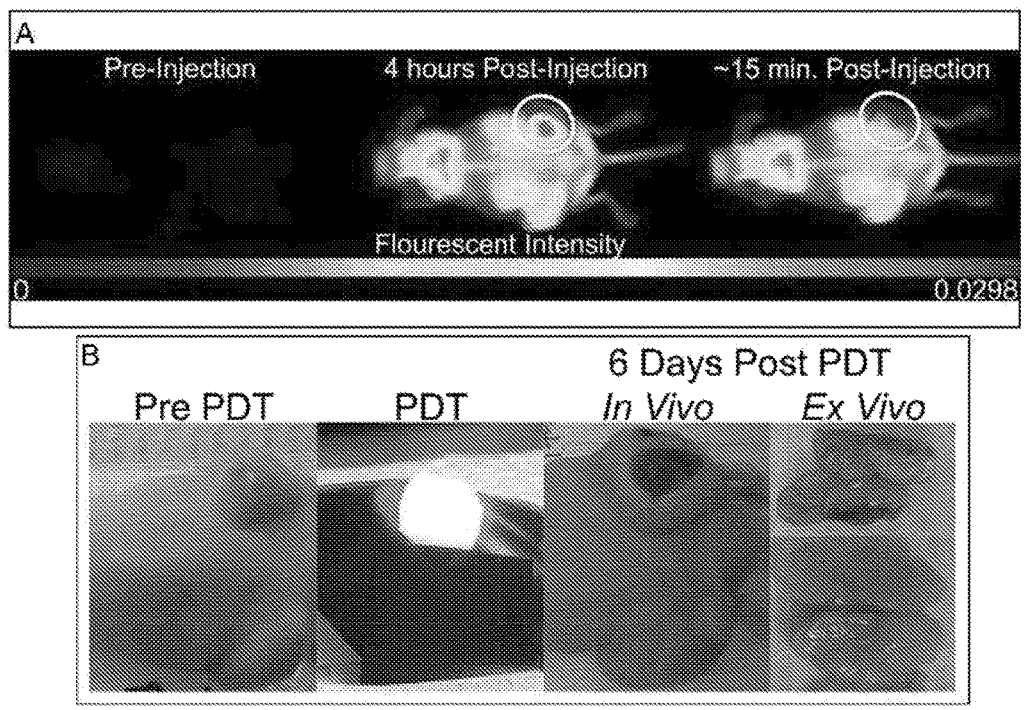
Figs. 6A-B

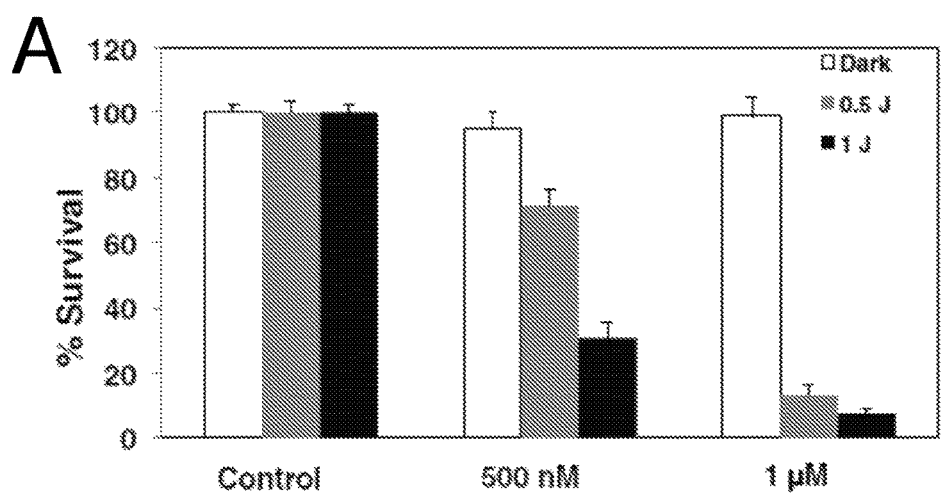
Fig. 10A
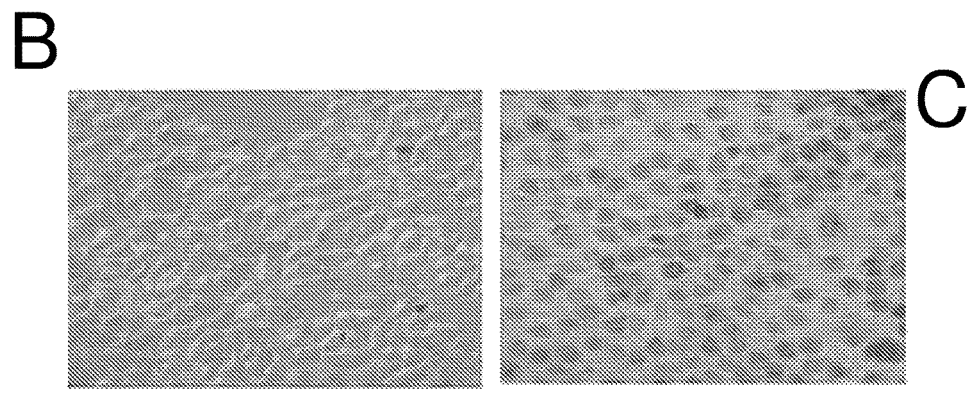
Figs. 10B-C

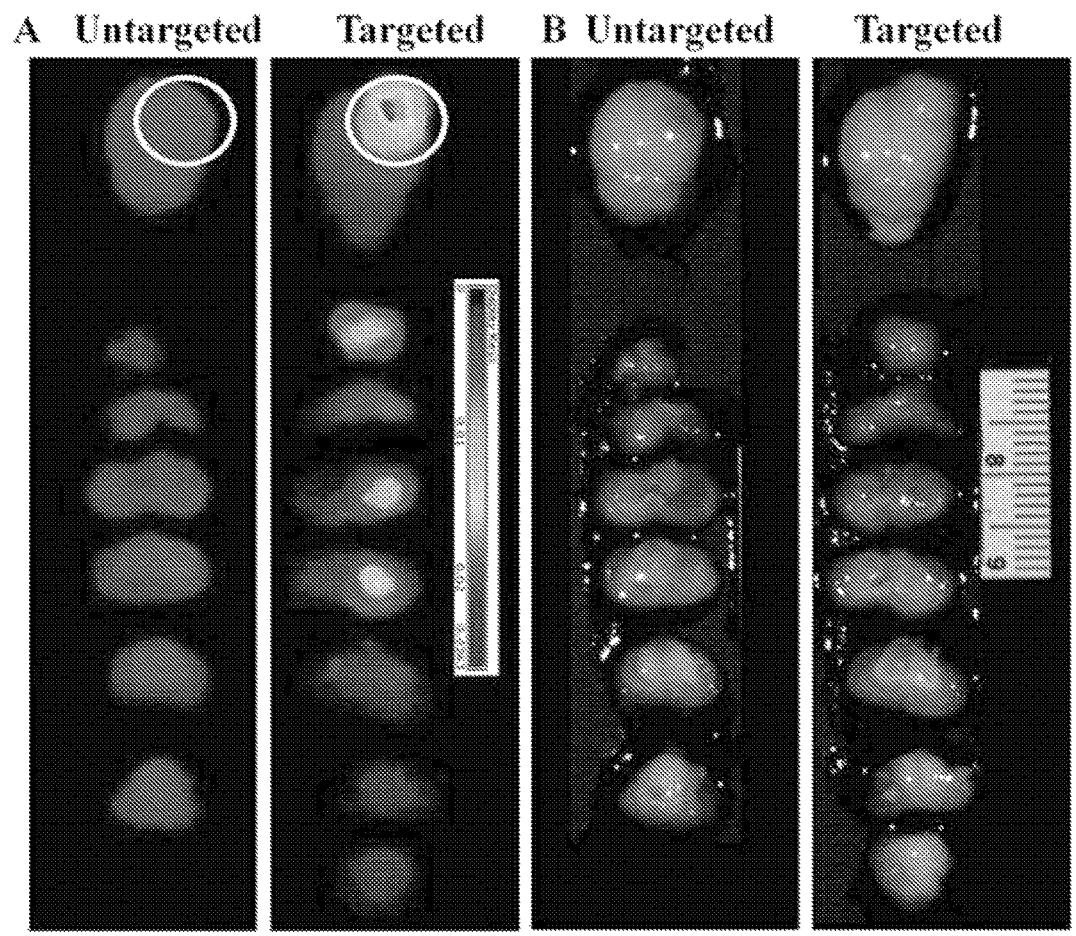
Figs. 12A-B

SEQUENCE LISTING

<160> NUMBER OF SEQ ID NOS: 1

<210> SEQ ID NO 1
<211> LENGTH: 12
<212> TYPE: PRT
<213> ORGANISM: Homo sapiens

<400> SEQUENCE: 1

Tyr His Trp Tyr Gly Tyr Thr Pro Gln Asn Val Ile
1               5                   10

TARGETED NANOPARTICLE CONJUGATES

RELATED APPLICATION

This application is a National Phase filing of PCT/US2012/106713, filed Feb. 6, 2012, which claims priority from U.S. Provisional Application No. 61/439,443, filed Feb. 4, 2011, the subject matter of which are incorporated herein by reference in their entirety.

TECHNICAL FIELD

This application relates to targeted nanoparticle conjugates and to the use of targeted nanoparticle conjugates for delivering hydrophobic therapeutic agents to targeted cells or tissue in a subject.

BACKGROUND

Inefficient delivery and poor uptake of therapeutic drugs to solid tumors hamper the efficacy of cancer treatments. Therefore, the "enhanced permeability and retention" (EPR) effect of solid tumors has been explored extensively as a target in the design of drug delivery systems. Solid tumors behave differently from normal tissues, having several abnormalities, such as leaky blood vessels and a poor lymph system. It is an important feature that nanosized particles can extravasate from the vasculature and passively accumulate in tumors. Inorganic nanoparticles, especially gold nanoparticles (Au NPs) with good biocompatibility, versatile surfaces, tunable sizes, and unique optical properties have received significant attention as drug delivery systems to improve targeting effect and efficacy for cancer treatments.

SUMMARY

This application relates to compositions that include targeted nanoparticle conjugates and to the use of the targeted nanoparticle conjugates for treating a disorder in a subject. In an aspect of the application, the targeted nanoparticle conjugate can include a polyethylene glycolylated (PEGylated) nanoparticle; at least one hydrophobic therapeutic agent coupled to the surface of the nanoparticle; and at least one targeting moiety coupled to polyethylene glycol of the nanoparticle for targeting the composition to a cell associated with a disorder.

In some aspects, the disorder is cancer and the at least one targeting moiety targets the composition to a cancer cell. The hydrophobic therapeutic agent can be an anti-cancer agent that has a log P value of about 1 to about 3. In one example, the anti-cancer agent is Phthalocyanine 4.

In other aspects, the at least one targeting moiety includes a polypeptide that binds to epidermal growth factor receptor (EGFR). The polypeptide can include an epidermal growth factor (EGF) peptide having the amino acid sequence of SEQ ID NO: 1.

Another aspect of the application relates to a composition for treating brain cancer. The composition includes a PEGylated gold nanoparticle; Phthalocyanine 4 conjugated to the PEGylated gold nanoparticle; and a polypeptide coupled to polyethylene glycol of the nanoparticle, the polypeptide binding EGFR. The polypeptide can consist of the amino acid sequence of SEQ ID NO: 1.

In some aspects, the composition upon systemic administration to the subject readily crosses the blood brain barrier and targets the brain cancer cells. The Phthalocyanine 4 can be readily up taken by the brain cancer cells upon targeting and upon uptake can be activated by light to cause cancer death or suppress cancer growth.

The application further relates to a method for treating brain cancer. The method includes administering systemically to a subject with brain cancer a therapeutically effective amount of a composition comprising PEGylated gold nanoparticles; Phthalocyanine 4 conjugated to the PEGylated gold nanoparticles; and EGF peptides consisting of the amino acid sequence of SEQ ID NO: 1 coupled to polyethylene glycol of the nanoparticles. The cancer cell administered the composition is then exposed to light, thereby inducing the cytotoxic effects of Phthalocyanine 4.

BRIEF DESCRIPTION OF THE DRAWINGS

FIG. 10 illustrates: (A) a graph showing PDT effect of the EGF-Au NP-Pc 4 conjugates on toxicity in light and dark after 4 h incubation measured with an MTT assay; brightfield images of the conjugate-incubated cancer cells before (B) and after (C) light exposure.

FIG. 12 illustrates fluorescence imaging of extracted brains with (A) tumors targeted with EGF-Au NP-Pc 4 conjugates compared to (B) untargeted Au NP-Pc 4 conjugates in brain tumor-bearing mice and the overlay of fluorescence and monochromatic images.

DETAILED DESCRIPTION

Figure 1:
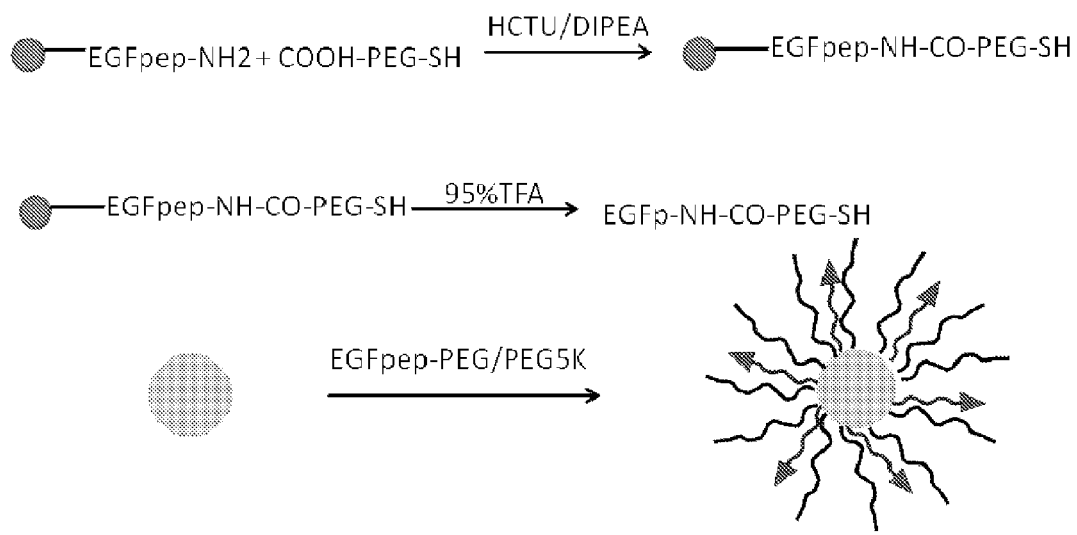
FIG. 1 is a schematic illustration of two-way synthesis of $EGF_{pep}$-Au nanoparticles. Dark circles stand for the resin; Light circles stand for gold nanoparticles; Lines stand for monofunctional PEG5K or for bifunctional PEG3K/7.5K/12K; Arrows stands for EGF peptide.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the term "imaging probe" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "targeting moiety" can refer to a molecule or molecules that are able to bind to and complex with a biomarker. The term can also refer to a functional group that serves to target or direct a therapeutic agent or anti-cancer agent to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

As used herein, the term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

As used herein, the term "nanoparticle" refers to any particle having a diameter of less than 1000 nanometers (nm). In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

As used herein, "log P" refers to the logarithm of the ratio of the concentrations of an unionized solute in solvent. Log P is also known as a measure of lipophilicity.

This application relates to targeted nanoparticle conjugates and methods of using the targeted nanoparticle conjugates to deliver a hydrophobic therapeutic agent to a targeted cell or tissue of a subject or mammal. The targeted nanoparticle conjugates can target and transiently interact with, bind to, and/or couple with a targeted cell or tissue and once interacting with, bound to, or coupled to the targeted cell or tissue advantageously facilitate delivery of a hydrophobic therapeutic agent within cell by, for example, receptor mediated endocytosis. This intercellular delivery of the therapeutic agent by targeted nanoparticles described herein was unexpected compared to similar nanoparticles that were not targeted to the cell or tissue as untargeted nanoparticle conjugates were found to be 10 fold less effective at delivering drugs into cells in vivo. Advantageously, the targeted nanoparticle conjugates can cross the blood brain barrier and have a size that allows the targeted nanoparticle conjugates to be readily excreted from the body after delivery of the hydrophobic therapeutic agent to the targeted cell.

In one example, the targeted nanoparticle conjugates can deliver a hydrophobic anti-cancer agent to a targeted cancer cell of a subject. Targeting the cancer cells resulting in selective killing of cancer cells while causing minimal damage to surrounding tissue.

The targeted nanoparticle conjugates can include a targeted nanoparticle and at least on hydrophobic therapeutic agent. The targeted nanoparticle can be coated with a plurality of polymer chains and at least some of the polymer chains are coupled to at least one cellular targeting moiety. In some embodiments, a first end of a polymer chain can be coupled and/or bound to a surface of the nanoparticle and a second opposite end that extends from the surface of the nanoparticle is coupled and/or bound to a targeting moiety. The targeting moiety can allow the targeted nanoparticle conjugates to transiently interact, couple, and/or bind to the targeted cell or tissue.

The polymer coating can provide a protective shell that increases the hydrophilicity of the nanoparticle and biocompatibility of the targeted nanoparticle conjugates and postpone and/or delay clearance of the targeted nanoparticle conjugates after delivery to the subject by reticular-endothelium system. The polymer coating also acts as an amphiphilic reservoir that can adsorb and stabilize hydrophobic therapeutic agents in aqueous medium and/or blood of the subject without the need to modify the structure of the therapeutic agent. The adsorption and stabilization of the hydrophobic therapeutic agent allows the hydrophobic therapeutic agent to be delivered to the targeted cell or tissue by the targeted nanoparticle conjugates and minimizes side effects.

In some embodiments, the nanoparticles used to form the targeted nanoparticle conjugates are quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but are not limited to, gold, silver, iron, cobalt, zinc, cadmium, nickel, gadolinium, chromium, copper, manganese, palladium, tin, and alloys and/or oxides thereof. In some embodiments, the nanoparticles can be magnetic nanoparticles. "Magnetic particles" refers to magnetically responsive particles that contain one or more metals or oxides or hydroxides thereof.

In some embodiments, the nanoparticles can have an average diameter of about 1 nm to about 30 nm. In other embodiment, the nanoparticles can have an average diameter of about 5 nm or less. Nanoparticles with an average or nominal diameter of about 5 nm or less can be readily cleared from the subject by reticular endothelium system after delivery of the hydrophobic therapeutic agent to the targeted cell or tissue.

The polymers used to coat the nanoparticles can include natural proteins, such as bovine serum albumin (BSA), biocompatible hydrophilic polymers, such as polyethylene glycol (PEG) or a PEG derivative, phospholipid-(PEG), lipids, and carbohydrates, such as dextran. Coatings of polymer may be applied or assembled in a variety of ways, such as by dipping, using a layer-by-layer technique, by self-assembly, or conjugation. Self-assembly refers to a process of spontaneous assembly of a higher order structure that relies on the natural attraction of the components of the higher order structure (e.g., molecules) for each other. Self-assembly typically occurs through random movements of the molecules and formation of bonds based on size, shape, composition, or chemical properties.

In one embodiment, the polymer coating can include polyethylene glycol (PEG). The PEG can be a heterobifunctional PEG, such as COOH-PEG-SH (MW 3000), and/or a monofunctional PEG, such as PEG-SH (MW 5000), that can readily bind to the nanoparticle to coat the nanoparticle. In some embodiments, the nanoparticle can be coated with a mixture of hetero-bifunctional PEG, such as COOH-PEG-SH (MW 3000), and monofunctional PEG, such as PEG-SH (MW 5000). The mixture can range in percent composition of hetero-bifunctional PEG to monofunctional PEG of about 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, and 99:1 respectively.

The targeting moiety can include any molecule, or complex of molecules, which is/are capable of targeting, interacting with, coupling with, and/or binding to an intracellular, cell surface, or extracellular biomarker of a cell or tissue. The biomarker can include, for example, a cellular protease, a kinase, a protein, a cell surface receptor, a lipid, and/or fatty acid. Other examples of biomarkers that the targeting moieties can target, interact with, couple with, and/or bind to include molecules associated with a particular disease. For example, the biomarkers can include cell surface receptors implicated in cancer development, such as epidermal growth factor receptor and transferrin receptor. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, a targeting moiety as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting moiety can be targeting peptide comprising an EGF peptide. The EGF peptide may comprise the amino acid sequence YHWYGYT-PQNVI-amide (SEQ ID NO: 1). The peptide may be synthesized by any method known in the art. For example, the EGF peptide may be synthesized manually using Fmoc protected amino acids (Peptides International, Louisville, Ky.) on rink-amide CLEAR resin (Peptides International, Louisville, Ky., 100-200 mesh size, 0.4 milliequivalents/gram). Fmoc amino acids (3 equiv.) can be coupled to the elongated chain with HCTU (1H-benzotriazolium-1-[bis(dimethylaminomethylene]-5-chloro-hexafluorophosphate-(1-),3-oxide) (3 equiv.), 6-Cl-HOBt (1-hydroxy-6-chlorobenzotriazole) (3 equiv.), and diisopropylethyamine (DIPEA, 6 equiv.) in DMF (N',N' dimethylformamide). Fmoc-deprotection may be achieved with 20% piperidine/DMF for 5 minutes incubation followed by 15-minute incubation. Each coupling and deprotection cycle can be followed by sequential washes with DMF (2×5 minute), isopropanol (IPA, 1×5 minute) and finally with methylene chloride (3×5 minutes). Each of the coupling and Fmoc-deprotection reactions can be monitored with ninhydrin tests. Discrete polyethyleneglycol units at the N-terminal can be introduced using Fmoc-8-amino-3,6-dioxaoctanoic acid (Peptide International). The peptides can be labeled with biotin on-resin with biotin-N-hydroxysuccinimide (Chem-Impex International, Wood Dale, Ill., 2 equiv.) and DIPEA (4 equiv.) for 1 hour in DMF. The global orthogonal deprotection and cleavage from resin can be achieved with incubation of dry resins in 95% trifluoroacetic acid (TFA), 2.5% water, and 2.5% triisopropylsilane for 3 hours. The peptides can be isolated with cold ether precipitation and centrifugation. The crude peptides can be purified using reverse phase HPLC through a C-18 column (Luna, 5 micron, 100 A mesh, 250 mm×10 mm, Phenomenex cat no. 00G-4252-N0) against a linear gradient of 5%-90% or 20%-60% acetonitrile against 0.1% trifluoroacetic acid in water at a flow rate of 2.5 mL per minute. Isolated peaks can be frozen and lyophilized to white flocculent powder. The peptides were characterized using MALDI mass spectrometry. Calculated for C75H98N18O10, expected molecular weight 1539.69; found 1540.12 $[M+H]^+$.

In other embodiments, the targeting moiety may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the composition to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

The targeting moiety can be coupled to the polymer chain prior to and/or after coupling of the polymer chain to the nanoparticle. For example, FIG. 1 is a schematic illustration of targeted nanoparticles that are prepared: (A) by coupling the targeting moiety to the polymer chain after the polymer chain is coupled to the nanoparticle; and (B) by coupling of the targeting moiety to the polymer chain prior to coupling the polymer chain to the nanoparticle.

The hydrophobic therapeutic agents, e.g., hydrophobic drugs and/or pharmacological compounds, can be loaded into and/or onto the polymer coating of the nanoparticles by encapsulation, absorption, adsorption, and/or non-covalent linkage of the hydrophobic therapeutic agent to or within the polymer matrix. The amount of hydrophobic therapeutic agent loaded onto the targeted nanoparticle can be controlled by changing the size of the nanoparticles or the composition of the polymer coating. Release of the hydrophobic therapeutic agent from the targeted nanoparticle may occur by desorption, diffusion through the polymer coating matrix, or polymer wall, and/or nanoparticle erosion, which can all be controlled by the type of the nanoparticle's polymer matrix, i.e., having it become swollen or degradable in the chosen microenvironment.

In some embodiments, the hydrophobic therapeutic agent can be a hydrophobic drug molecule that has a positive log P value. A hydrophobic therapeutic agent with a positive log P can be readily adsorbed into the polymer coating and stabilized in aqueous medium and/or blood of the subject without the need to modify the structure of the therapeutic agent. The adsorption and stabilization of the hydrophobic therapeutic agent allows the therapeutic agent to be delivered to the targeted cell or tissue and minimize side effects.

In other embodiments, the hydrophobic therapeutic agent can have a log P of about 1 to about 5. In still other embodiments, the hydrophobic therapeutic agent can have a log P of about 1 to about 3.

In some embodiments, the hydrophobic therapeutic agent can have an amino or amine functionality. Hydrophobic therapeutic agents with an amine functionality may be attached to the nanoparticle surface through electrostatic interactions. For example, anions attached to nanoparticle surface in aqueous solution, such as chloride anions, can bind to a protonated amine of the hydrophobic therapeutic agent. At physiological pH values, almost all amines of the hydrophobic therapeutic agent can protonated and provide coulomb bonding to the surface of the nanoparticles.

By way of example, a PEG coating can be covalently bound to the surface of a gold nanoparticle. The PEG coating can adsorb a hydrophobic therapeutic agent and hold the hydrophobic therapeutic agent in place while agent is transported to the target site. Van der Waals interactions can additionally stabilize the hydrophobic therapeutic agent adsorbed by the PEG.

Examples of hydrophobic therapeutic agents that can be adsorbed into the polymer coating and that have a positive log P are porphyrins and phthalocyanines, such as phthalocyanine 4 (Pc 4) and 5-aminolevulinic acid (5-ALA), rosiglitazone, and pioglitazone. Phthalocyanines, such as Pc4, can be used in photodynamic therapy (PDT). Pc4 is relatively photostable and virtually non-toxic. 5-aminolevulinic acid (5-ALA) leads to intracellular accumulation of fluorescent porphyrins, which can be used to monitor tumor margins. 5-ALA has also been used for photodynamic therapy (PDT) of gliomas with some success (Stummer, W. et al. J Neurooncol. 2008, 87(1):103-9.).

In some embodiments, the hydrophobic therapeutic agent is released from the nanoparticle once it reaches the target. Drug release can be induced by a thermodynamic driving force that drives the hydrophobic molecule from the amphiphilic environment of the polymer coating into any less polar site that may be offered for a long enough time. The hydrophobic therapeutic agent may be driven into the apolar center of the cell membranes and subsequently taken up into the targeted cell.

In another aspect of the application, the targeted nanoparticle conjugates can be formulated as pharmaceutical compositions. Formulation of pharmaceutical composition for use in the modes of administration noted below (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

For example, pharmaceutical compositions of the present application can contain can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose Examples of formulations for parenteral administration can include aqueous solutions of the composition in water-soluble form, for example, water-soluble salts and alkaline solutions. Especially preferred salts are maleate, fumarate, succinate, S,S tartrate, or R,R tartrate. In addition, suspensions of the composition as appropriate oily injection suspensions can be administered. Aqueous injection suspensions can contain substances that increase the viscosity of the suspension, such as sodium carboxymethyl cellulose, sorbitol and/or dextran. Optionally, the suspension may also contain stabilizers.

Formulations for topical administration to the skin include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

The above described targeted nanoparticle conjugates can be used in a method for treating a disorder in a subject. The disorder can include diseased cells. The cells can include a diseased cell or healthy cell that is derived from, or a part of, various tissue types, such as neuronal tissue (including both neuron and glia), connective tissue, hepatic tissue, pancreatic tissue, kidney tissue, bone marrow tissue, cardiac tissue, retinal tissue, intestinal tissue, lung tissue, endothelium tissue, cartilage, skeletal muscle, cardiac muscle, other cardiac tissue that is not muscle, smooth muscle, bone, tendon, ligament, adipose tissue and skin. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc.

In some embodiments, a therapeutically effective amount of the targeted nanoparticle conjugates can be administered in vivo to a subject to treat the subject. The targeted nanoparticle conjugates may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. For example, the targeted nanoparticle conjugates may be introduced into the central nervous system by any suitable route, including intraventricular injection, intrathecal injection, or intraventricular injection via an intraventricular catheter that is attached to a reservoir.

The targeted nanoparticle conjugates can also be delivered systematically (e.g., intra-venously), regionally, or locally (e.g., intra- or peri-tumoral injection) by, for example, intra-arterial, intra-tumoral, intra-venous, parenteral, intra-pneural cavity, topical, oral or local administration, as well as subcutaneous, intra-zacheral (e.g., by aerosol), or transmucosal (e.g., voccal, bladder, vaginal, uterine, rectal, nasal, mucosal). If delivery of the targeted nanoparticle conjugates to the brain is desired, the targeted nanoparticles can be injected into an artery of the carotid system of arteries (e.g., occipital artery, auricular artery, temporal artery, cerebral artery, maxillary artery etc.). As discussed above, the targeted nanoparticle conjugates can be formulated as a pharmaceutical composition for in vivo administration.

The targeted nanoparticle conjugates can be administered to the subject at an amount effective to provide a desired result(s) and to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The targeted nanoparticle conjugates can be administered in a variety of unit dosage forms, depending upon the particular cell or tissue being treated, the general medical condition of each subject, the method of administration, and the like. Details on dosages are well described in the scientific literature. The exact amount and concentration of the targeted nanoparticle conjugates, or the "effective dose", can be routinely determined (e.g., by a medical practitioner). The "dosing regimen" will depend upon a variety of factors, such as whether the cell or tissue to be treated is disseminated or local, the general state of the subject's health, the subject's age, and the like. Using guidelines describing alternative dosing regimens, e.g., from the use of other agents and compositions, the skilled artisan can readily determine by routine trials the optimal effective concentrations of the composition.

In some aspects of the application, the targeted nanoparticle conjugates can be formulated and used in a photodynamic therapy to treat cancer or tumor (e.g., brain cancer or tumors). Photodynamic therapy (PDT) is a site specific treatment modality that requires the presence of a photosensitizer, light, and adequate amounts of molecular oxygen to destroy targeted tumors (Grossweiner, Li, The sicence of phototherapy. Springer: The Netherlands, 2005). Upon illumination, a photoactivated sensitizer transfers energy to molecular oxygen that leads to the generation of singlet oxygen ($O^2$) and other reactive oxygen species (ROS), which initiate apoptosis and oxidative damage to cancer cells. Only the cells that are exposed simultaneously to the PDT drug (which is non-toxic in the dark) and light are destroyed while surrounding healthy, non-targeted and non-irradiated cells are spared from photodamage. Furthermore, the fluorescence of the photosensitizer molecules enables simultaneous diagnostic optical imaging that can be used to guide the PDT cancer treatment.

The targeted nanoparticle conjugates formulated for PDT treatment method can include PEGylated gold nanoparticles (Au NPs) that are modified with a cancer cell targeting moiety (e.g., EGF targeting peptide) and that are conjugated to a hydrophobic PDT therapeutic agent (e.g., Pc4) that is spacially encaged and photophysically quenched through adsorption on the PEGylated nanoparticles. The nanoparticles (NPs) can include gold nanoparticles that have a diameter about 5 nm or less to allow efficient excretion via renal clearance after delivery of the hydrophobic PDT therapeutic agent. The PEGylated nanoparticles can each have an average or nominal diameter of about 38 nm. About 10 to about 50, e.g., about 20-30, hydrophobic PDT therapeutic agents can be adsorbed on each nanoparticle.

The targeted nanoparticles containing the hydrophobic PDT therapeutic agent can be administered to a subject with cancer (e.g., brain cancer) by systemic administration, such as intravenous administration. Upon administration, the targeted nanoparticle conjugates can localize to and/or accumulate at the site of the targeted tumor or cancer. Transient binding and/or interaction of the targeted nanoparticle conjugates with the targeted cancer or tumor cells (e.g., glioma cells) allows the hydrophobic PDT therapeutic agent to be delivered to and take up by the targeted cells by, for example, endocytosis with virtually no uptake of the nanoparticles. This uptake is specific to the targeted cancer cells, which allows selective targeting of the cancer cells in the subject by the targeted nanoparticle conjugates.

Following administration and localization of the targeted nanoparticle conjugates as well as uptake of the hydrophobic PDT therapeutic agent by the targeted cancer cells, the targeted cancer cells can be exposed to therapeutic amount of light that causes cancer cell damage and/or suppression of cancer cell growth. The light, which is capable of activating the PDT therapeutic agent can delivered to the targeted cancer cells using, using for example, semiconductor laser, dye laser, optical parametric oscillator or the like. It will be appreciated that any source light can be used as long as the light excites the hydrophobic PDT therapeutic agent.

The following examples are for the purpose of illustration only and are not intended to limit the scope of the claims, which are appended hereto.

Example 1

Figure 2:
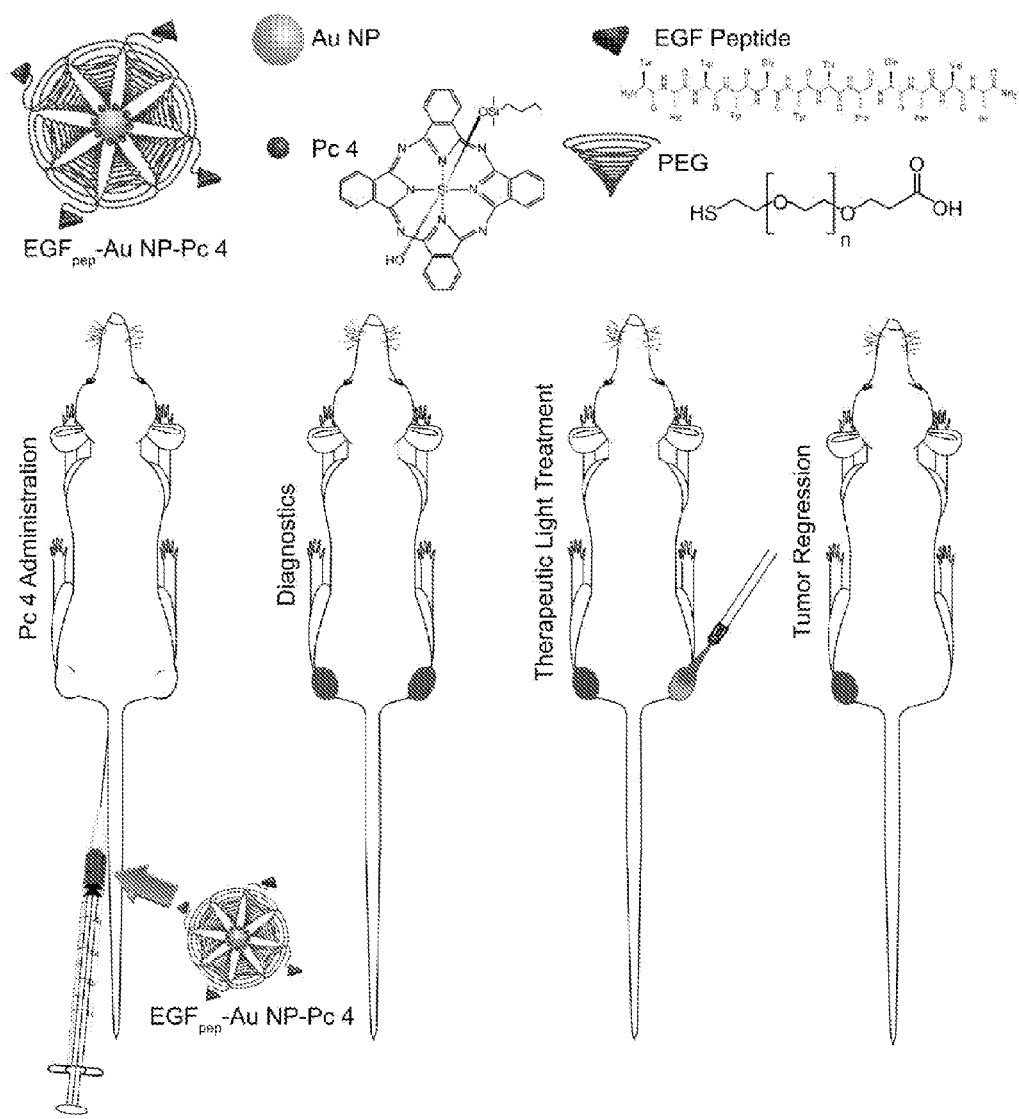
FIG. 2 is a schematic of: (A) a diagram of the construction of $EGF_{pep}$-Au NP-Pc 4; and (B) a procedure for photodynamic.

This example shows EGF peptide modified Au NPs in combination with the PDT drug Pc 4 to achieve an enhanced targeting effect in subcutaneous tumor bearing mice as illustrated in FIG. 2. In this example, we utilized glioblastoma multiforme (GBM) tumors, which are the most common type of malignant primary brain cancer, by using a rat GBM cell line 9L.E29 engineered to overexpress human EGFR. In vitro studies suggest that the drug is mainly released into cancer cells by membrane-mediated diffusion. In vitro studies also show differences in cellular localization that cause an enhanced PDT effect. In vivo studies further show that the $EGF_{pep}$-Au NP-Pc 4 complexes improve accumulation of Pc 4 in subcutaneous tumors, and following exposure to therapeutic light, cause tumor damage and/or suppression of tumor growth.

Methods

Synthesis of the EGF Peptide YHWYGYTPQNVI-amide (SEQ ID NO: 1)

The EGF peptide YHWYGYTPQNVI-amide (SEQ ID NO: 1), was synthesized manually using Fmoc protected amino acids on Rink-amide resin as previously reported. The crude peptides were purified using reverse phase HPLC through a C18 column. The peptides were characterized using MALDI mass spectrometry. Calculated for $C_{75}H_{98}N_{18}O_{10}$, expected molecular weight 1539.69; found 1540.12 $[M+H]^+$.

Synthesis and Characterization of EGF Au NP-Pc 4 Complexes

Au NPs were synthesized based on a modified Brust-Schiffrin method. The NPs were etched and shielded by the mixture of mPEG-SH (MW 5000) and HS-PEG-COOH (MW 3000) with 4:1 mole ratio for 48 hours. The carboxyl functionalized Au NPs were purified by centrifugation with 100,000 Dalton molecular weight cutoff filtration membranes. The EGF peptide was conjugated on the carboxyl functionalized NP surface through the amide bond. The conjugates were characterized as previously reported.

Quantification of the Complexes' Cellular Uptake of Au NPs and Pc 4

9L.E29 cells were cultured in 60 mm×15 mm cell culture dishes and incubated with either $EGF_{pep}$-Au NP-Pc 4, or Au NP-Pc 4 for 4 and 24 hours. Pc 4 in the cells was extracted with ethyl acetate and quantified by UV-Vis spectroscopy. After digesting the cells by 70% $HNO_3$, the Au NPs were quantified by graphite furnace atomic absorption spectroscopy (GFAAS), as previously reported.

Cell Confocal Imaging Studies

9L.E29 cells were seeded on coverslips and incubated with EGFpep-Au NP-Pc 4 or free Pc 4 at $1×10^{-6}$ mol/L of Pc 4. For EEA1 immunofluorescent slides, cells were washed three times with PBS and fixed using 4% paraformaldehyde for 15 minutes. After permeabilization with 100% methanol for 5 minutes at room temperature, the coverslips were washed with PBS. The primary antibody anti-EEA1 (Cell Signaling Technology: Danvers, Mass.; cat. 2411) was incubated with the cells for 1 hour. After rinsing three times with PBS, the secondary antibody goat anti-rabbit-Alexa 488 was added and incubated for 1 hour. The coverslips were rinsed with PBS three times and mounted with aqueous mounting solution (containing DAPI). For the LysoTracker and MitoTracker studies, live cells were washed three times with PBS, and stained with either LysoTracker (Invitrogen: Grand Island, N.Y.; cat. L7526) at a concentration of 75 nM in DMEM or MitoTracker (Invitrogen: Grand Island, N.Y.; cat. M7514) at a concentration of 100 nM in DMEM, for 30 minutes. After staining, cells were washed three times with PBS and fixed using 2% paraformaldehyde, and 0.1% glutaraldehyde in PBS. After being rinsed three times with PBS, the coverslips were mounted with aqueous mounting solution (with DAPI). One laser scanning confocal microscope (Leica; TCS-SP) was used to capture the EEA1 fluorescent images, and another laser scanning confocal microscope (Zeiss; LSM 510 META) was used to capture the LysoTracker and MitoTracker fluorescent images.

Cell Viability and Phototoxicity of the EGF Au NP-Pc 4 Complexes

The average cell viability in the dark and under light exposure was evaluated by the MTT assay. $EGF_{pep}$-Au NP-Pc 4 and free Pc 4 were incubated with the cells and were irradiated under light (>550 nm) at 0.5 J cm² and 1 J·cm², respectively. The plates were incubated with the yellow tetrazolium salt MTT labeling reagent. After purple formazan crystals were formed, the absorbance at 550 nm (for the formazan salt formation) and 690 nm as the reference wavelength was measured with 8 replicates used for each condition.

Tumor Implantation

Engineered rat glioma 9L.E29 cancer cell lines were subcutaneously implanted in the flank of athymic mice (about $3×10^5$ cells/implant) and animal experiments were performed according to IACUC policies and guidelines of the animal care and use committee at Case Western Reserve University as previously reported.

Biodistribution Experiments and In vivo Fluorescence Imaging

Mice with flank tumors were anaesthetized with isoflurane and injected intravenously via the tail with either EGF$_{pep}$-Au NP-Pc 4 or Au NP-Pc 4 complexes at a dosage of 1 mg·kg$^{-1}$ of Pc 4 per total mouse body weight. Fluorescent multispectral images were obtained using the Maestro In vivo Imaging System (Cambridge Research and Instrumentation, Inc., Woburn, Mass.). The gold content was analyzed by GFAAS in a GTA-110 (Varian, Inc., Palo Alto, Calif.).

Histology Studies with Silver Enhancement Staining and H&E Staining

Tissue samples were fixed in 4% paraformaldehyde at room temperature and embedded in the paraffin blocks. The tissue sections were stained with SPI-Mark™ silver enhancement kit (SPI Supplies Division of Structure Probe, Inc.: West Chester, Pa.; cat. 04180-AB) to allow visualization of the Au NPs by deposition of silver onto the gold particles by reduction. Histological preparation and visualization were conducted as previously described.

PDT Treatment of In vivo Subcutaneous Tumors

Mice with flank tumors were anaesthetized with isoflurane and injected intravenously via the tail with either EGF$_{pep}$-Au NP-Pc 4 or Au NP-Pc 4. Three separate treatment regimens were followed: mice were injected at a dosage of 0.5 mg·kg$^{-1}$ and treated with 150 J·cm$^2$ of laser light (672 nm), mice were injected at a dosage of 1 mg·kg$^{-1}$ and treated with 50 J·cm$^2$ of laser light (672 nm), or mice were injected at a dosage of 1 mg·kg$^{-1}$ and treated with 150 J·cm$^2$ of laser light (672 nm). The mice with flank tumors were imaged before injection (pre-injection), immediately following injection (0 hours), and every hour after up to 4 hours. At this time the mice were treated with their respective dosage of laser illumination (672 nm at either 50 or 150 J·cm$^2$). The mice were then imaged post-treatment and allowed to recover. A day after the injection the mice were imaged, and continued to be imaged every 24 hours until mice were euthanized due to tumor size (unless euthanized at 24 hours). Imaging and analysis followed was conducted as previously described.

Results

Figure 3A:
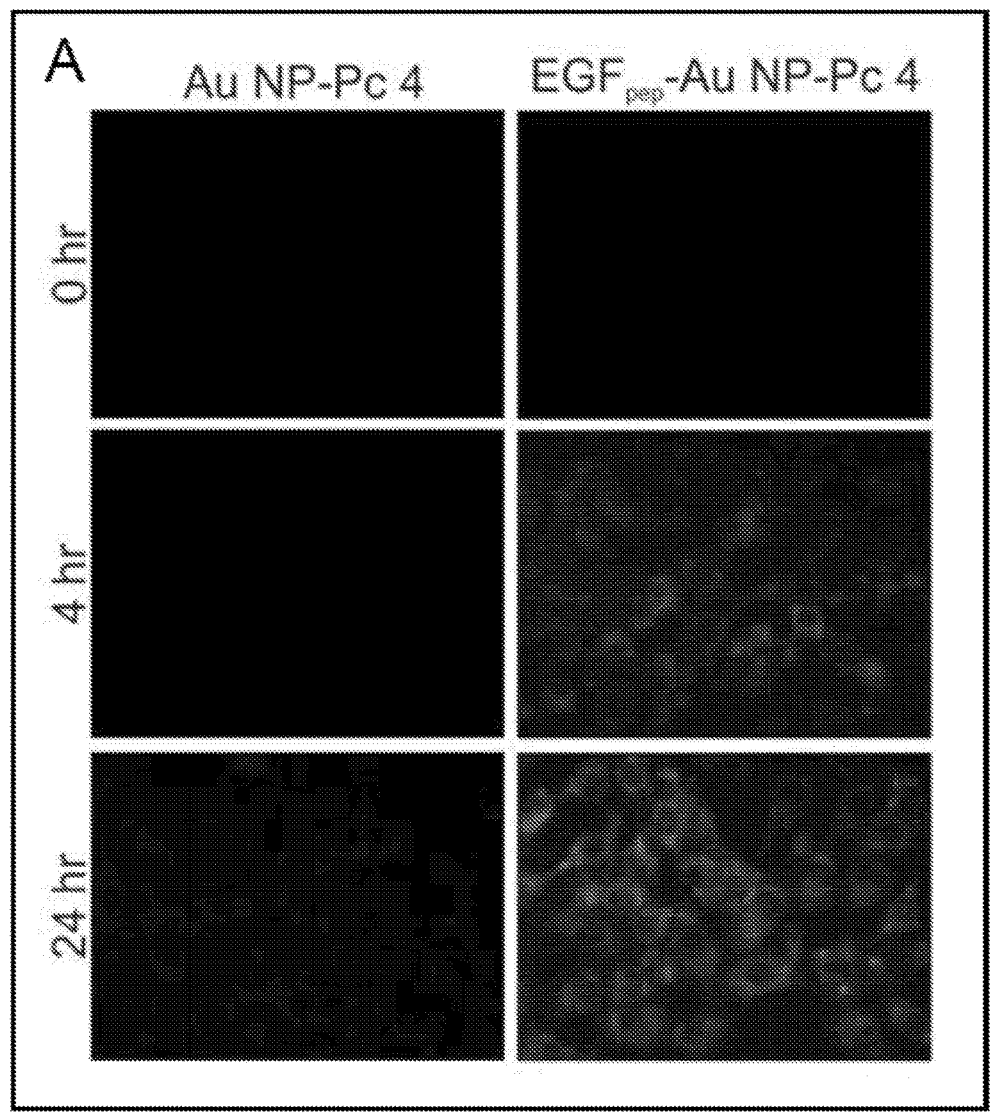
FIG. 3 illustrates (A) epi-fluorescent images of in vitro uptake and increasing accumulation of $EGF_{pep}$-Au NP-Pc 4 in 9L.E29 cells incubated with either EGFpep-Au NP-Pc 4, or Au NP-Pc 4 at $1\times10^{-6}$ mol/L of Pc 4 taken over time at 40× magnification; (B) a graph showing quantification of Pc 4 (mols) per Au NP (mols) in 9L.E29 cells over time; and (C) a graph showing quantification of Au (μg) per 9L.E29 cell over time.

First, we examined the uptake and accumulation of EGF$_{pep}$-Au NP-Pc 4 as compared to Au NP-Pc 4 in 9L.E29 cells using the intrinsic fluorescence of Pc 4 and elemental characteristics of the gold (FIG. 3). As shown in FIG. 3A, little Pc 4 was absorbed into cells incubated with Au NP-Pc 4 over a 24 hour period (left panel). In contrast, significant uptake of Pc 4 was visualized after a mere 4 hours of incubation with EGF$_{pep}$-Au NP-Pc 4 (right panel). To determine whether the EGF peptide was responsible for this increased uptake of Pc 4 in vitro, we conducted a peptide competition assay. Cells were pre-incubated with increasing concentrations of free EGF peptide for 4 hours. Quantification of Pc 4 fluorescence demonstrated that the drug delivery pathway was blocked, suggesting that EGF$_{pep}$-Au NP-Pc 4 interacted with EGF receptors to deliver Pc 4 via receptor-mediated endocytosis rather than macro pinocytosis.

Figure 3B:
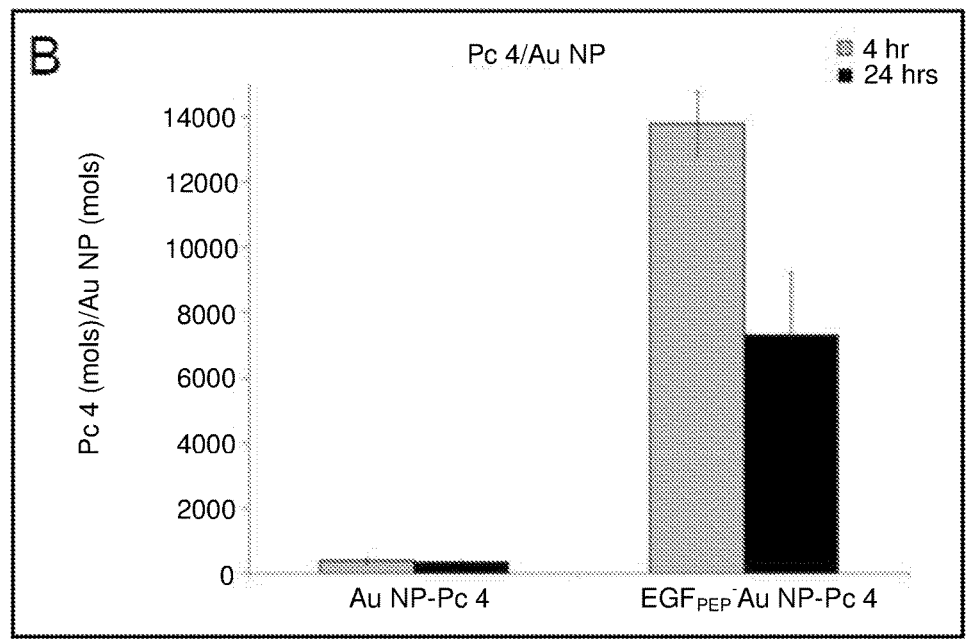
Figure 3C:
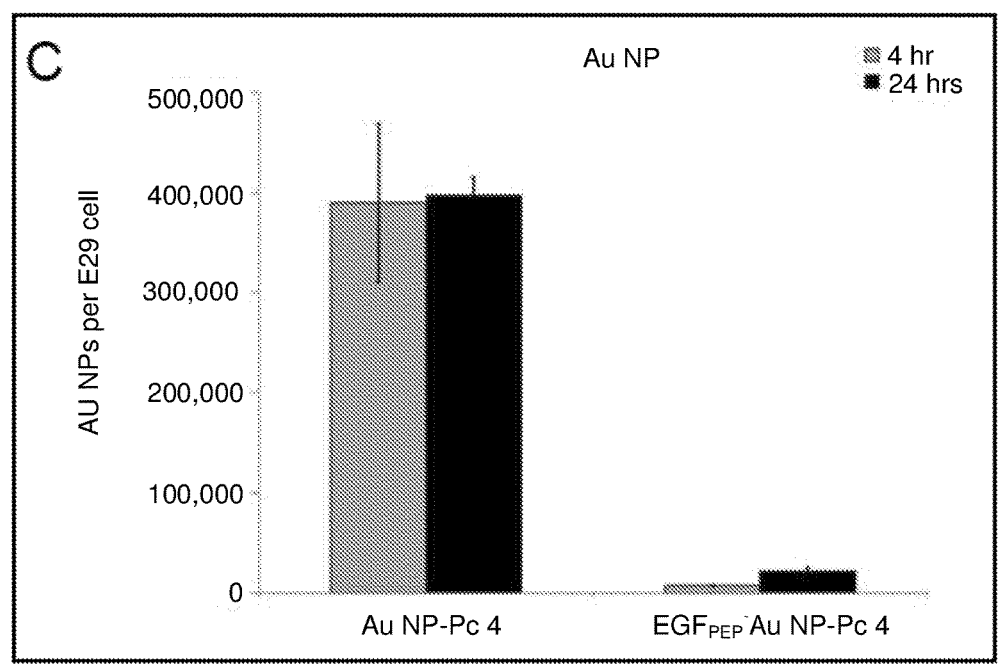

Quantification of the in vitro results showed that after only 4 hours of incubation, EGF$_{pep}$-Au NP-Pc 4 produced an overall 35-fold increase of the amount of Pc 4 per Au NP delivered to cancer cells when compared to Au NP-Pc 4 (FIG. 3B). It is hypothesized that the EGF receptor targeted peptide acts as an anchor to allow the EGF-Au NP-Pc 4 to dock at the cancer cell's surface like a ferry and unload its cargo of Pc 4 into the cell due to Pc 4's hydrophobic interaction with the membrane. This anchoring effect is transient and EGF$_{pep}$-Au NP-Pc 4 can dissociate from the cell to be excreted by the body or, in the case of in vitro experiments, can be washed away during rinsing. This is demonstrated by the fact that EGF$_{pep}$-Au NP-Pc 4 shows a 47-fold decreased uptake of the Au NPs in comparison to Au NP-Pc 4 at 4 hours (FIG. 3C). Therefore EGF-Au NP-Pc 4 is able to unload more Pc 4 per Au NP into cancer cells at 4 hours post-incubation. The exact mechanism for this ferrying action is unknown and under current investigation.

Figure 4A:
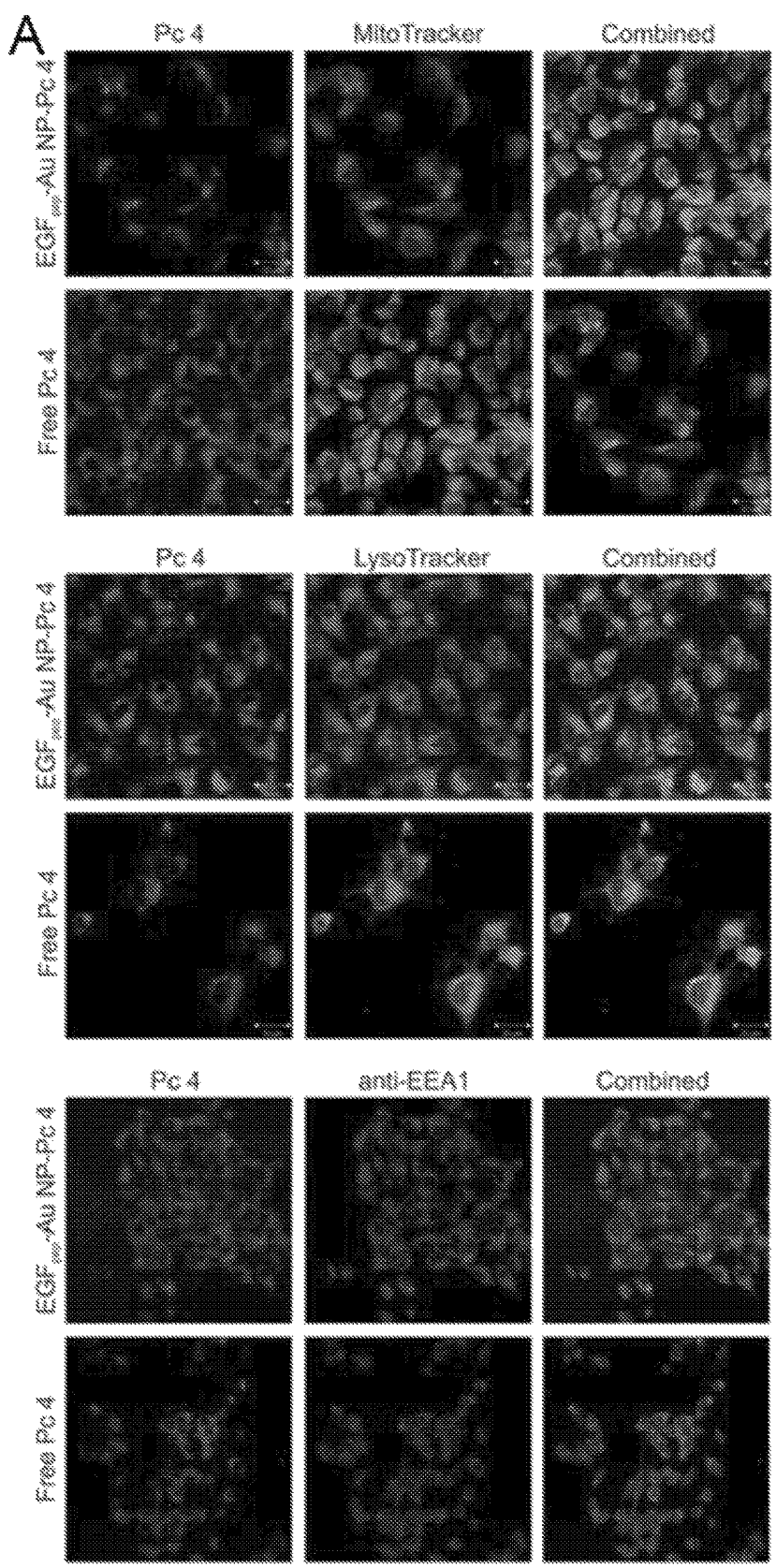
FIG. 4 illustrates: (A) confocal imaging of 9L.E29 cells seeded on coverslips and incubated with $EGF_{pep}$-Au NP-Pc 4 or free Pc 4 at $1\times10^{-6}$ mol/L of Pc 4, and either LysoTracker (for lysosomes), MitoTracker (for mitochondria), or EEA1 antibodies (for early endosomes); (B) a graph of an MTT assay showing cytotoxicity associated with $EGF_{pep}$-Au NP-Pc 4 and Pc 4 in the dark and under different light exposures on 9L.E29 cells; and (C) a viability assay (Trypan blue staining) showing cytotoxicity associated with $EGF_{pep}$-Au NP-Pc 4 and free Pc 4 under different light exposures and concentrations of Pc 4 on 9L.E29 cells.

Once the Au NPs were modified with the EGF peptides, receptor-mediated drug delivery appeared to dominate the Pc 4 uptake and accumulation as suggested by FIG. 3A. To determine the precise subcellular localization of Pc 4, we treated cells overexpressing EGFR with either EGF$_{pep}$-Au NP-Pc 4 or free Pc 4 (1 µM), counterstained with antibodies against the discrete organelles of the cell, and visualized the co-localization using confocal fluorescence microscopy (FIG. 4A). Free Pc 4 is known to localize mainly in mitochondria with some additional localization within lysosomes. However, Pc 4 in cells treated with EGF$_{pep}$-Au NP-Pc 4 localized strikingly in organelles associated with receptor-mediated endocytosis, specifically within the early endosomes and lysosomes (FIG. 4A).

Figure 4B:
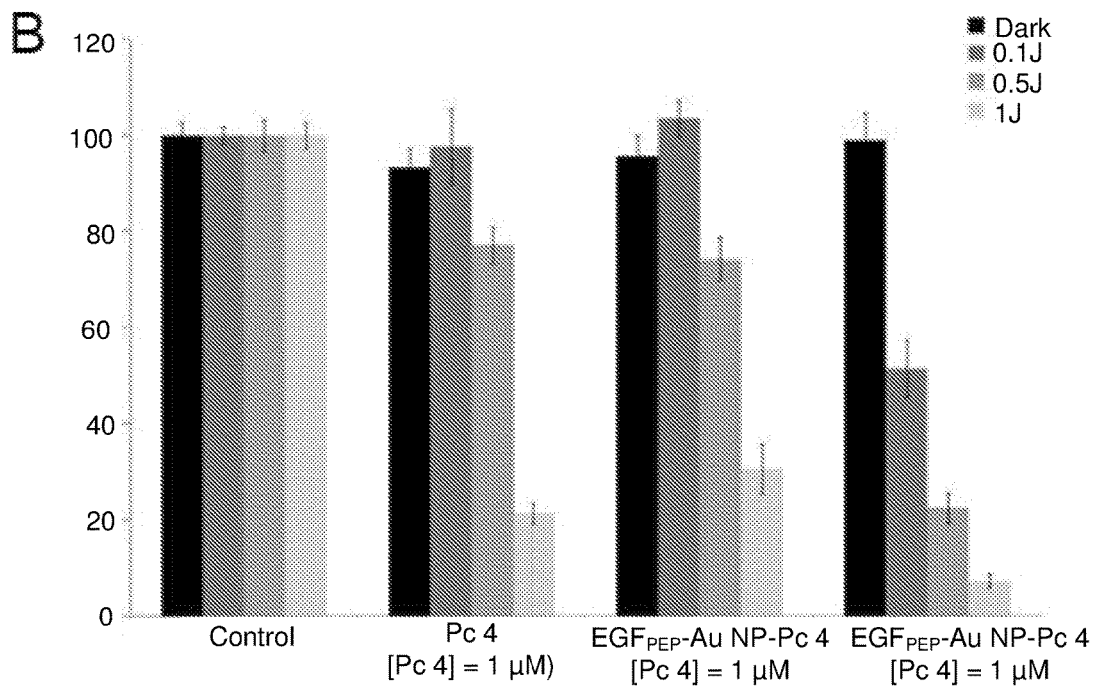

The dark toxicity and phototoxicity of EGF$_{pep}$-Au NP-Pc 4 was evaluated by MTT assay (FIG. 4B). No dark toxicity was observed during the incubation with EGF$_{pep}$-Au NP-Pc 4. EGF$_{pep}$-Au NP-Pc 4 showed excellent phototoxicity at 1 µM of Pc 4 concentration, as over 90% of cancer cells were destroyed with 1 J·cm$^2$ light exposure. The PDT effect of the complexes could even be obtained at a very low fluence with nearly 50% of the cancer cells being killed at only 0.1 J·cm$^2$ irradiation. EGF$_{pep}$-Au NP-Pc 4 has a similar cell killing efficiency to that of free Pc 4 at only half of the concentration of free Pc 4 (0.5 µM) and the same light illumination of 1 J·cm$^2$. In vitro PDT also showed that at half the power of light illumination (0.5 J·cm$^2$ light) and the same concentration of Pc 4 (1 µM), EGF$_{pep}$-Au NP-Pc 4 killed 57% more cancer cells than free Pc 4. This suggests that EGF$_{pep}$-Au NP-Pc 4 causes a similar PDT effect at half the concentration of Pc 4 and the same power of laser illumination or a better PDT effect at the same concentration of Pc 4 and half the power of laser illumination.

Figure 4C:
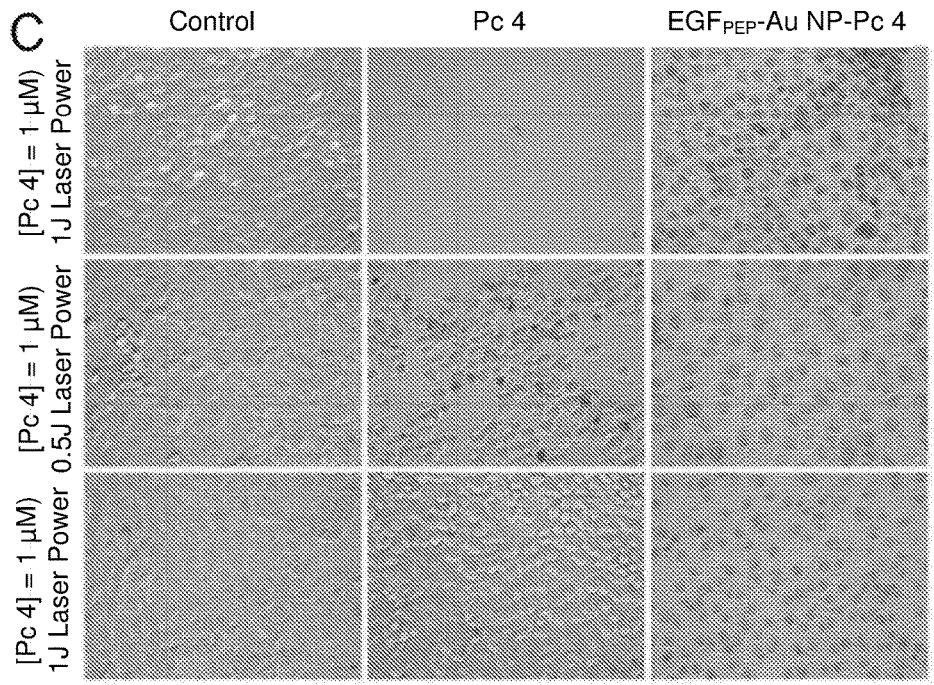

Cell viability assays using Trypan blue for EGF$_{pep}$-Au NP-Pc 4 treated cells further illustrated this point (FIG. 4C), showing not only an increase in the number of dead cancer cells, but possibly different pathways of cell death. At 1 µM of Pc 4 and 1 J·cm$^2$ of laser power, free Pc 4 caused most cancer cells to die very quickly and the cells no longer adhered to the plate and were washed away before the remainder were stained. The cancer cells incubated with EGF$_{pep}$-Au NP-Pc 4 seemed to undergo a more controlled apoptotic cell death causing the cells to swell, remain adherent to the plate, and were stained uniformly with membrane impermeant trypan blue stain.

The biodistribution and clearance of the EGF$_{pep}$-Au NP-Pc 4 were evaluated in vivo over a 7 day period. No side effects from the complexes were observed in the animals as monitored by behavior and general appearance. Biodistribution of Pc 4 and Au NPs delivered by EGF$_{pep}$-Au NP-Pc 4 in vivo was visualized and quantified by fluorescence imaging, histological staining, and GFAAS analysis of ex vivo dissected organs (FIG. 5A).

Figure 5A:
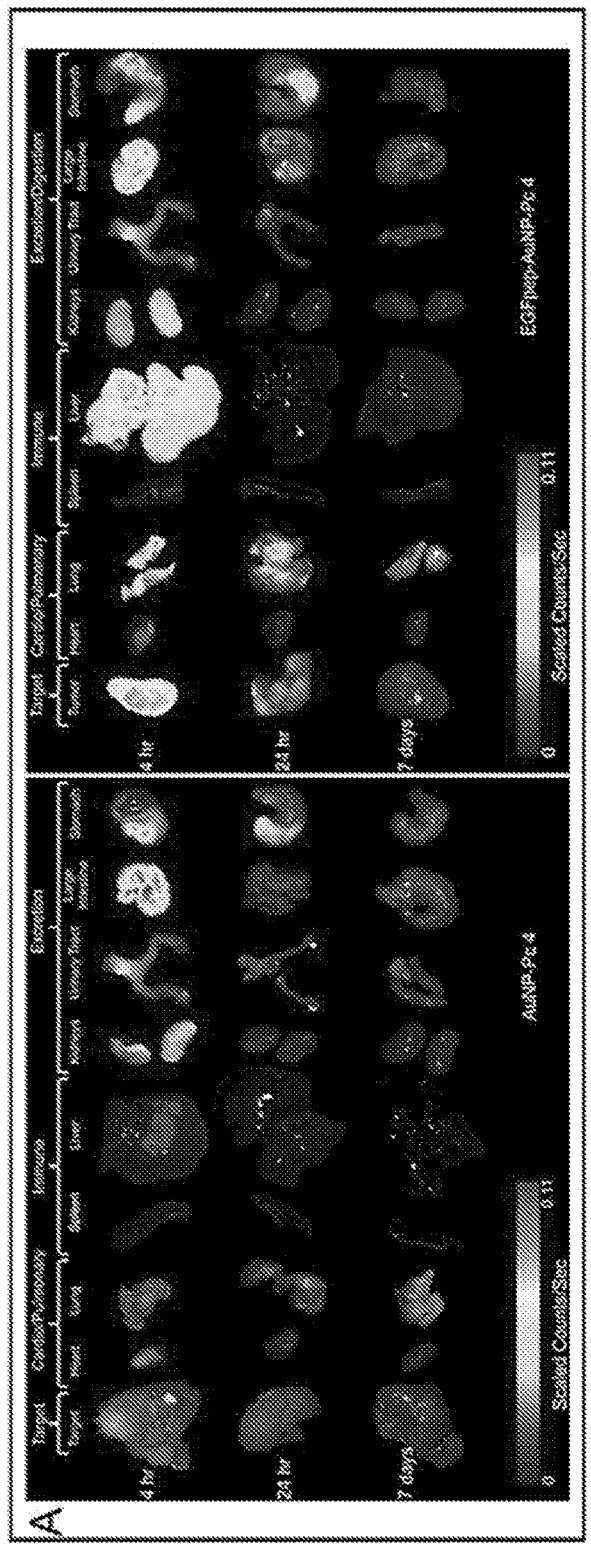
FIG. 5 illustrates: (A) evenly scaled fluorescent images of ex vivo organs overlayed on corresponding black and white pictures of biodistribution of $EGF_{pep}$-Au NP-Pc 4 Mice injected with Au NP-Pc 4 or $EGF_{pep}$-Au NP-Pc 4 (at a concentration of 1 mg·kg$^{-1}$ of Pc 4), euthanized at 4 hours, 24 hours, or 7 days post-injection; (B) silver enhanced staining of ex vivo organs for visualization of Au NPs; (C) a graph of fluorescence biodistribution for Pc 4 content (in average RFUs) of ex vivo organs of all mice injected with $EGF_{pep}$-Au NP-Pc 4, for each time point n≥3; and (d) Au NP biodistribution for Au NP content (in μg of Au) of ex vivo organs of all mice injected with $EGF_{pep}$-Au NP-Pc 4, for each time point n≥3.
Figure 5B:
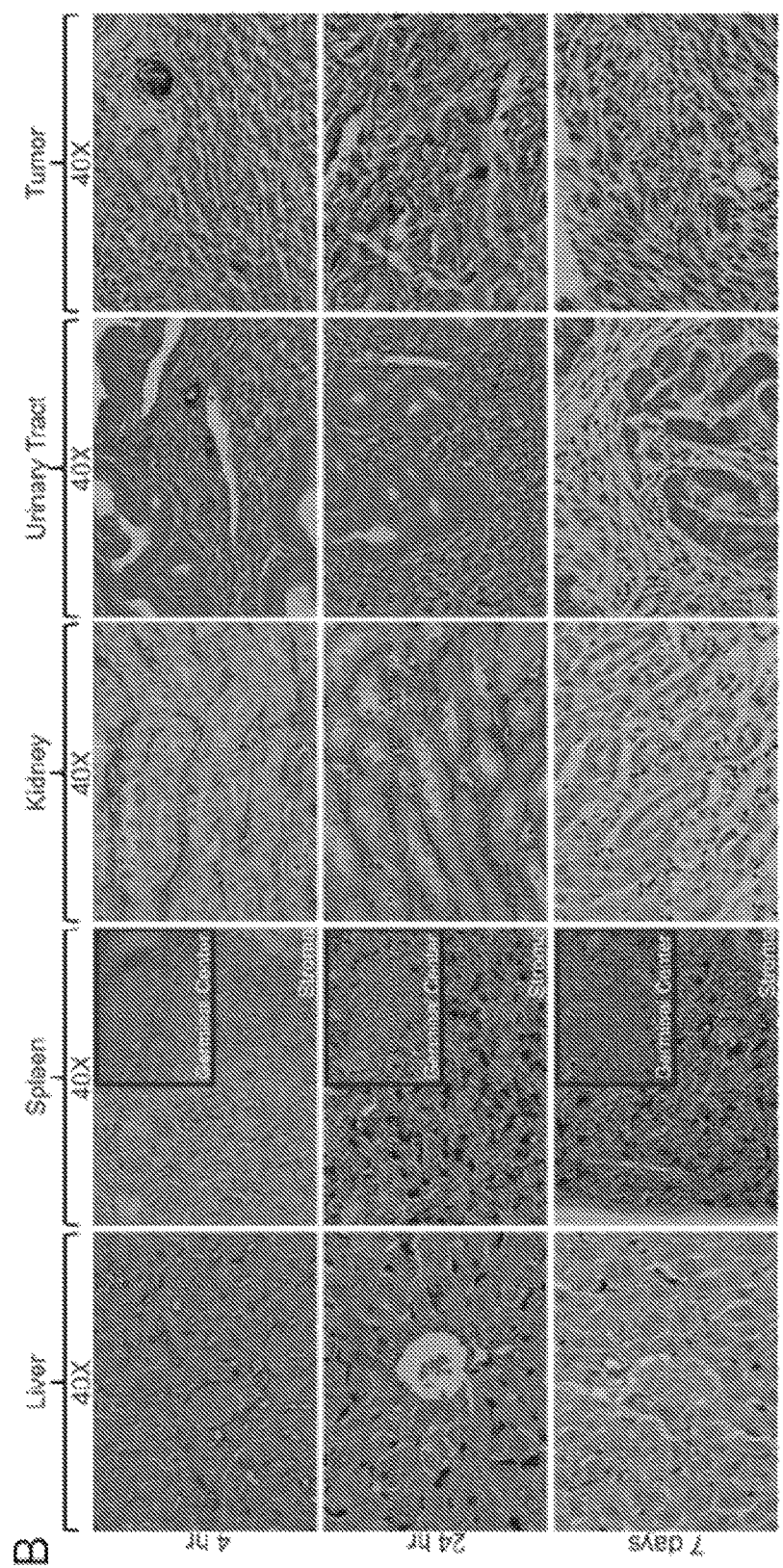

Examining Pc 4 fluorescence from mice treated with Au NP-Pc 4 showed Au NP-Pc 4 appeared to nonspecifically accumulate Pc 4 as early as 4 hours after administration in large intestines, stomach and excretory tract (FIG. 5A, left panel). Little to no specific uptake of the drug was observed in the tumor. In comparison, $EGF_{pep}$-Au NP-Pc 4 differentially accumulated in the tumor and liver (FIG. 5A, right panel). EGF-Au NP-Pc 4 appeared to accumulate Au NPs as early as 4 hours after administration in liver and spleen tissues by silver staining (FIG. 5B). Instead of Au NPs accumulating in the liver over time, a relatively fast decrease of the NPs was observed in 7 days. At 4 hours, the histology samples of the spleen showed little uptake of the Au NPs. However, the spleen showed an overall increase of the Au NPs after 7 days, which suggests the spleen may play an important role in the clearance of the Au NPs.

Next, the Au NPs in the tumor tissues were investigated by silver enhanced staining and H&E staining. Similar to the untargeted complexes, the Au NPs delivered by the targeted complexes were found to accumulate around the vasculature of the tumor at 4 hours postinjection (FIG. 5B). The $EGF_{pep}$-Au NP-Pc 4 complexes showed a different Au NP biodistribution in the tumors after 24 hours post-injection (FIG. 5B). An accumulation of Au NPs around the cancer cells' membranes in the tumor was observed in contrast to the randomly distributed untargeted NPs. Thus the selective targeting effect of the $EGF_{pep}$-Au NP-Pc 4 complexes correlated to the binding ability of their EGF peptides to EGFRs on the cancer cells. By 7 days post-injection, very few Au NPs were found in tumor tissues or surrounding vasculature.

Figure 5C:
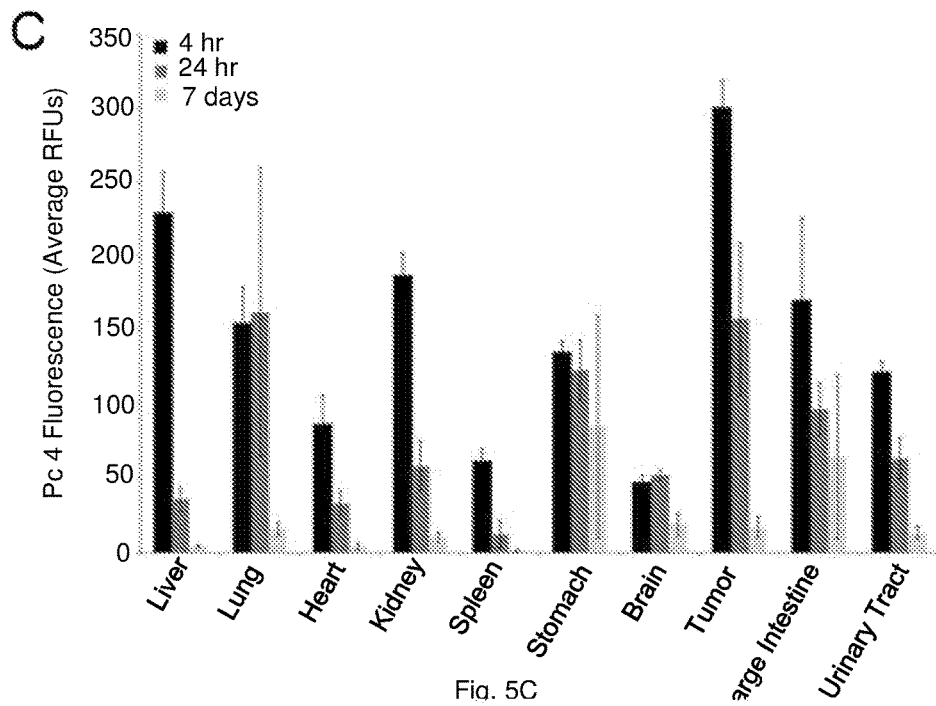

Quantification of Pc 4 fluorescence intensities demonstrated the rapid clearance of Pc 4 from the body over the 7 day period (FIG. 5C). After 24 hours, the fluorescence decreased significantly in all of the organs and 7 days after the injection no obvious fluorescence could be observed, which indicated rapid excretion of the drug from the body. This suggests the excretion of Pc 4 was through the hepatobiliary system and by renal clearance.

Figure 5D:
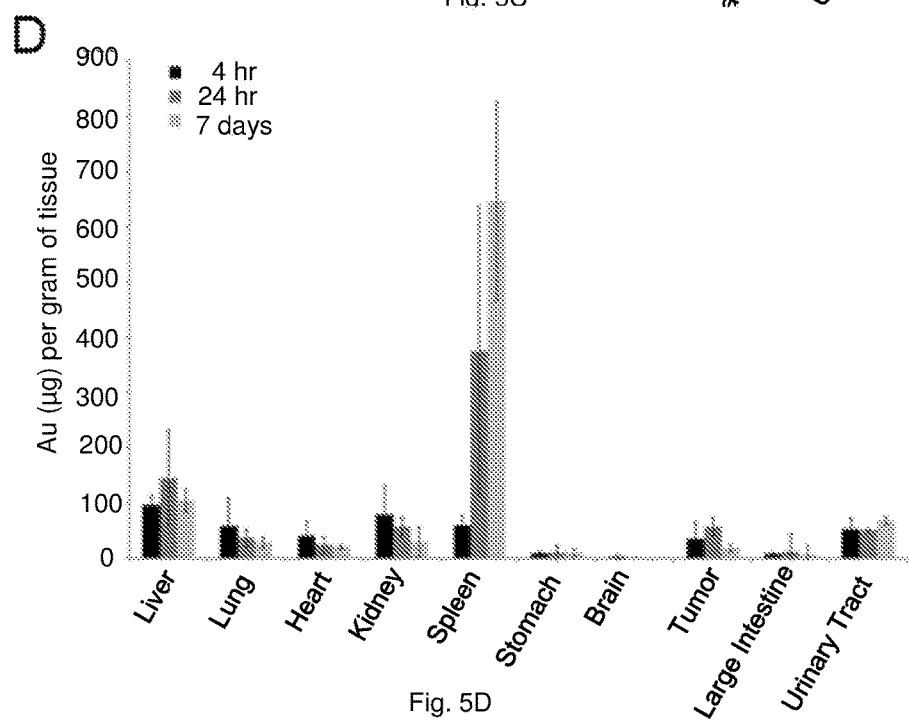

Au NPs showed a relatively long half-life in the blood. After 4 hours post injection, 204.9 µg ml$^{-1}$ or about 50% of the injected dose (ID) of the targeted Au NPs remained in the blood. Meanwhile, about 16 µg g$^{-1}$ or less than 20% of the injected dose of the targeted Au NPs was taken up by the liver and the spleen (FIG. 5D). This indicated that the EGF peptide modified Au NPs could minimize uptake by the reticular-endothelium system (RES) resulting in prolonged blood circulation. After 24 hours post-injection, 60.4 µg ml$^{-1}$ or about 13.5% ID of the NPs was found in the blood with increased accumulation in liver and spleen. After 7 days post-injection, a significant decrease of the NPs was observed in all the organs except the spleen.

While the Au NPs were found in the excretion organs such as the kidney, urinary tract, large intestine and stomach, the Au NPs were also found in the urine and feces samples from the mice injected with the complexes. A significant portion of Au NPs remained circulating in the blood within 24 hours post-injection and greater than 50 µg Au/g of sample was detected in the urine samples. As the Au NP accumulation in the blood dropped to 0.5% ID after 7 days, the Au NP accumulation in the urine decreased as well to about 20 µg Au/g of sample. This indicated that the Au NPs could be excreted by renal clearance, and that the clearance rate was correlated to the circulation of the Au NPs in the body. The existence of Au NPs in the feces, stomach and large intestine indicated another important excretion pathway. At 4 hours post injection, although the NPs existed in the stomach and large intestine, only a few of the Au NPs were detected in the feces samples. After 24 hours, there was an increase in the amount of Au NPs in the feces samples. Indicating the excretion of the NPs was through the hepatobiliary system as well.

Figure 6C:
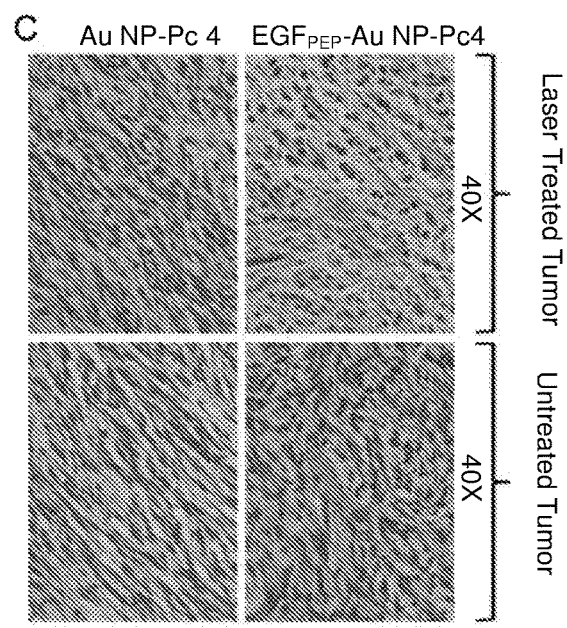
FIG. 6 illustrates: (A) fluorescence images of an $EGF_{pep}$-Au NP-Pc 4 injected mouse showing accumulation of Pc 4 and its subsequent drop in intensity after being activated by laser light; (B) photographs of an $EGF_{pep}$-Au NP-Pc 4 injected and PDT treated mouse (The left tumor was not treated with light); (C) Hematoxylin and Eosin staining of Paraffin fixed tumor sections from animals sacrificed at 4 hours after injection of either Au NP-Pc 4, or $EGF_{pep}$-Au NP-Pc 4 and either treated or not treated with laser light, visualized at 40× magnification; and (D) a graph showing Pc 4 fluorescence (RFU) per μg of Au in 9L.E29 tumors over time in mice injected intravenously with either $EGF_{pep}$-Au NP-Pc 4 or Au NP-Pc 4 complexes at a dosage of 1 mg·kg$^{-1}$ of Pc 4 and ex vivo tumor tissues.

The PDT efficacy of $EGF_{pep}$-Au NP-Pc 4 was studied in the animals (FIG. 6). Four hours was used as a satisfactory treatment time for PDT efficacy because it showed the greatest accumulation of the drug over the shortest circulation time. Conventional PDT uses 1 mg·kg$^{-1}$ of Pc 4 and 150 J·cm$^2$ of laser power. However, using this standard of care resulted in heavy edema at the site of the treated tumor, extremely high toxicity, and sometimes death in animals within 24 hours of undergoing treatment (data not shown). The treatment regime was modified to avoid these unsatisfactory results. Therefore, three additional treatment regimens were employed as described above. At half of the conventional dosage (0.5 mg·kg$^{-1}$) and the a third of conventional laser power (50 J·cm$^2$), the targeted complexes showed excellent phototoxicity and subsequent damage to the subcutaneous tumors. The treated tumors showed immediate loss of fluorescence indicating photobleaching from the activation of Pc 4, and swelling around the treated site only minutes after treatment (FIG. 6A-B). Between 24 hours and 7 days, the treated tumors showed visible signs of tissue damage (FIG. 6B) and necrosis was observed within the tissues after resection and histologic staining (FIG. 6C). Some animals showed visible shrinkage in the size of the tumor. However, shrinkage was not maintained over 4 days because of the ensuing edema and the remaining tumor cells continued to proliferate.

Figure 6D:
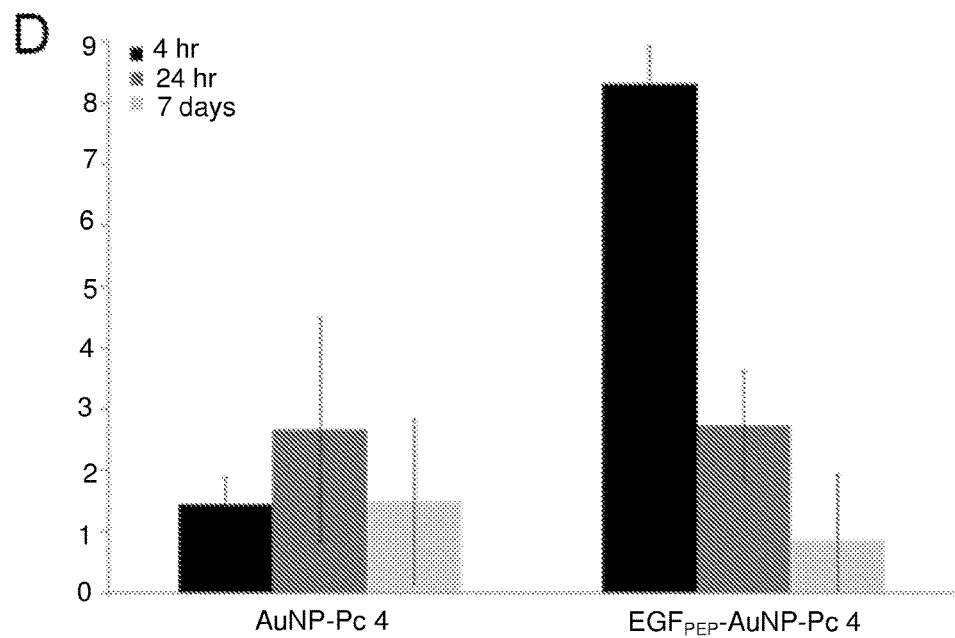

This difference in PDT efficacy may be explained by the quantification of both Pc 4 fluorescence and elemental gold in subcutaneous tumors (FIG. 6C-D). Results confirmed that $EGF_{pep}$-Au NP-Pc 4 showed an overall 5.7-fold increase of the drug fluorescence intensity per nanoparticle in comparison to Au NP-Pc 4 as shown in the ex vivo Pc 4 fluorescence per Au NP graph (FIG. 6D). By 24 hours, both untargeted and targeted complexes show nearly the same amount of drug per nanoparticle (FIG. 6D). However, at 24 hours the number of Au NPs (in terms of µg of gold) and the amount of Pc 4 (in terms of average intensity) delivered by targeted complexes are both respectively twice that delivered by the untargeted complexes, but by 7 days both targeted and untargeted complexes show approximately the same number of Au NPs and amount of Pc 4. This proves that the targeted complexes deliver more Pc 4 per Au NP to subcutaneous tumors at both 4 hours and 24 hours post-injection, while maintaining a similar excretion rate as the untargeted complexes within 7 days.

Figure 7:
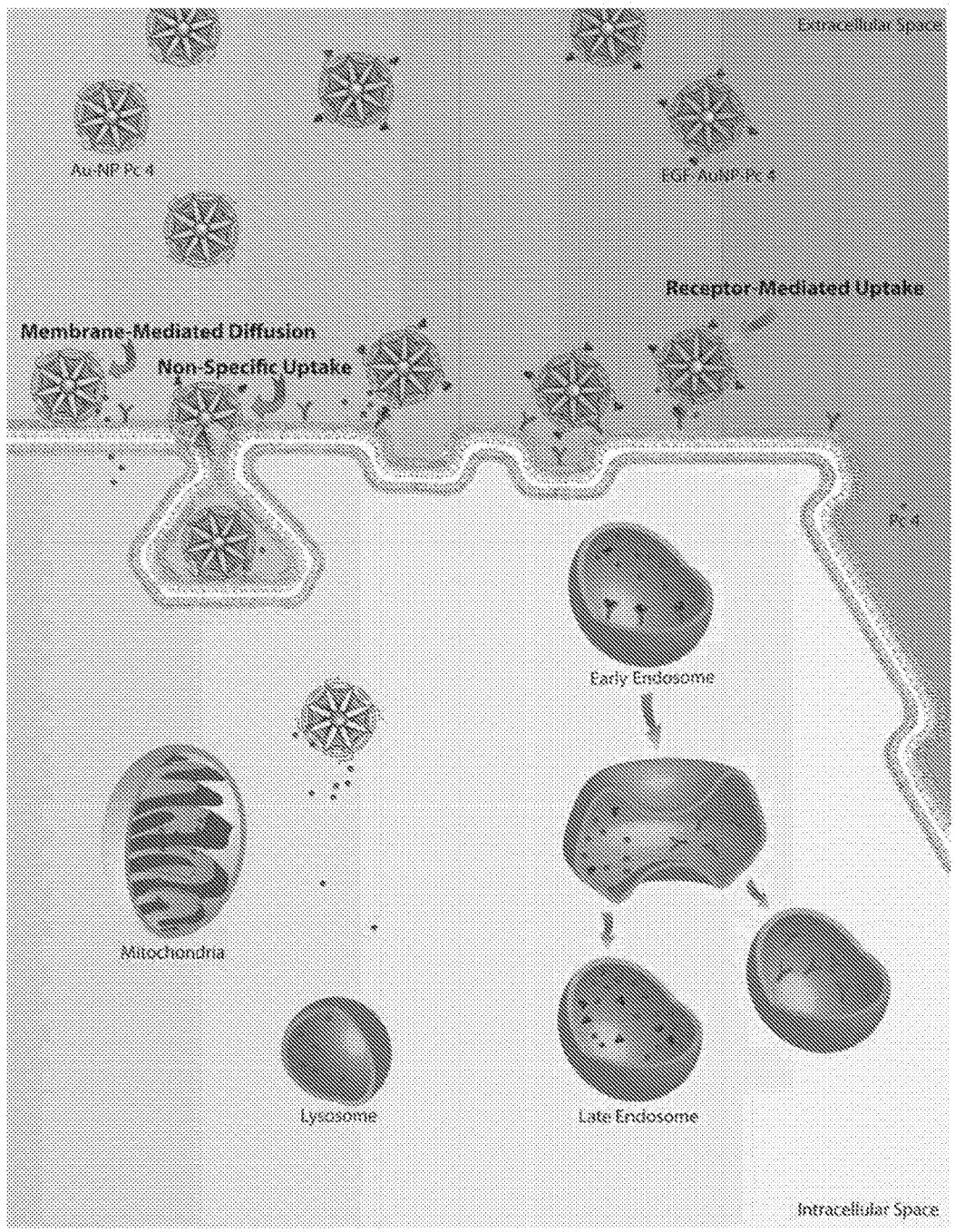
FIG. 7 is a schematic illustration of a model of redistribution showing the difference in Pc 4 uptake when delivered by EGF$_{pep}$-Au NP-Pc 4 that may account for differences in cell death pathways.

This example shows a targeted PDT drug delivery system by EGF peptide modified Au NPs studied using GBM cell lines both in vitro and in vivo. In vitro results show that our EGFR targeted complexes deliver Pc 4 to cancer cells without much uptake of the Au NPs themselves and provide increased uptake of Pc 4 per Au NP when compared to their untargeted counterparts. Results also show that the EGFR targeting peptide provides active targeting to cancer cells and alters the subcellular delivery pathway to early endosomes with improved delivery to lysosomes when compared to free Pc 4 (FIG. 7). Similar differences in cellular localization were previously shown to improve the photodynamic cell killing effect of Pc 4. This was confirmed by our results, which show that $EGF_{pep}$-Au NP-Pc 4 kills cancer cells more efficiently at half the concentration of free Pc 4 with the same amount of light irradiation. These results indicate that our EGFR targeted Au NPs can deliver Pc 4 to cancer cells more efficiently than untargeted complexes and cause increased cell death when compared to free Pc 4.

The circulation and clearance of the complexes in vivo was also evaluated within 7 days post-injection, and both the Au NPs and the drug showed a rapid clearance from the body in only 7 days. In vivo uptake studies indicated that the targeted complexes showed efficient drug release to subcutaneous tumors. The targeted complexes also improved the drug accumulation and therefore the selectivity to cancer cells in the subcutaneous tumors. Histology confirmed these results, showing improved adherence of Au NPs around cancer cells in tumors, which was consistent with the uptake studies of both Pc 4 and Au NPs. Even at a decreased dosage of 0.5 mg·kg$^{-1}$ of Pc 4 and 150 J·cm$^2$ of laser power, targeted complexes showed swelling around the treated tumor within minutes and caused visible signs of disruption of tumor growth as well as necrosis within days. These results indicate that targeting Pc 4 to cancer specific biomarkers gives better control over the bioavailability of Pc 4 and the release of Pc 4 into tumors. This will be of importance when transitioning to use EGF$_{pep}$-Au NP-Pc 4 for treatment of orthotopic tumors. Overall, the use of EGF$_{pep}$-Au NP-Pc 4 results in good therapeutic efficacy in tumors with low drug dosages, and decreased systemic side-effects.

Example 2

In the example, we demonstrate the rational design of a noncovalent Au NP drug-delivery platform which can cross the blood-brain-barrier/blood-brain-tumor barrier (BBB/BBTB) and selectively deliver therapeutic drugs to brain glioma tumors for PDT.

Methods

Au NPs were synthesized based on a modified Brust-Schiffrin method. The untargeted Au NP-Pc 4 conjugates were synthesized as reported and coated with mPEG-SH (MW 5000, Laysan Bio). To synthesize the targeted conjugates, Au NPs were etched and shielded by the mixture of mPEG-SH (MW 5000) and HS-PEG-COOH (MW 3000, Rapp Polymere) with a 4:1 ratio for 48 h. The carboxyl-functionalized Au NPs were purified by centrifugation with 50 000 Dalton-molecular-weight cutoff filtration membranes. The EGF peptide was attached on the carboxyl-functionalized NP surface through the amide bond. COOH— groups on the Au NPs were activated with EDC (1-ethyl-3-[3 dimethylaminopropyl]-carbodiimide) and Sulfo-NHS (N-hydroxysulfosuccinimide) in MES (2-[morpholino]ethanesulfonic acid) buffer at pH 4.7 for 15 min at room temperature. Then the buffer pH was increased immediately above 7 using concentrated PBS (phosphate-buffered saline). The Sulfo-NHS-activated NPs were well mixed with the EGF peptide at 1:1 ratio for 4 h at room temperature. Excess reactants were separated from the EGF peptide functionalized Au NPs (EGF-Au NPs) by centrifugation with 50 000 Dalton-molecular-weight cutoff membranes. The purified EGF-Au NPs were redissolved in chloroform and a 40-fold excess Pc 4 was added into the solution. After 48 h mixing at room temperature, the solvent was removed under vacuum. The EGF-Au NP-Pc 4 conjugates were suspended in aqueous solution and purified by centrifugation and 200 nm pore filters.

The average cell viability in the dark and under light exposure was evaluated by the MTT assay (Cell Proliferation Kit I by Roche). 9L.E29 rat glioma cancer cells, engineered to overexpress EGFR, were added (10 000 per well) in three 96-well plates and incubated for 24 h at 37° C. and 5% $CO_2$. The EGF-Au NP-Pc 4 conjugates and free Pc 4 were incubated with the cells in the dark for 4 hours. After washing three times, one plate was placed in the dark. The other two plates were irradiated under light of wavelength>550 nm at 0.5 J cm$^{-2}$ and 1 J cm$^{-2}$, respectively. The plates were incubated for another 24 h and 10 µL yellow tetrazolium salt MTT labeling reagent was added into each well. After 4 h incubation, the purple formazan crystals were formed by metabolic active cells. 100 µL of the solubilization solution per well was added to dissolve the cells and placed into the incubator overnight. The absorbance at 550 nm (the formazan salt) and 690 nm as reference wavelength was measured with a Tecan Infinite 200 microplate reader. 8 replicates were used for each condition.

Pc 4 in the cells was extracted with ethyl acetate and quantified with UV-vis spectroscopy. After digesting the cells with 70% $HNO_3$, Au NPs were quantified with graphite furnace atomic absorption spectroscopy (GFAAS). And localization of Au NPs in cells was detected by transmission electron microscopy (TEM). After 24 h incubation with the conjugates, the cells were fixed in 2.5% glutaraldehyde for 1 h after incubation with the conjugates. After washes with PBS, the samples were stained with 2% osmium tetroxide and 0.5% uranyl acetate. The samples were gradually dehydrated in ethanol and embedded in Epon-Propylene oxide. Thin sections were obtained with an ultramicrotome and deposited onto TEM grids. The images were taken on a JEOL JEM-1200 EX electron microscope.

Animal experiments were performed according to IACUC policies and guidelines of the animal care and use committee at Case Western Reserve University. Female athymic mice were obtained from the Athymic Animal Core Facility of the Cancer Research Center of Case Western Reserve University. Human glioma (Gli36 Δ 5) cancer cell lines were implanted on the right parietal lobe of the posterior of the brain using a stereotactic rig designed for mice Animals were continuously monitored for any signs of discomfort, and tumors were allowed to grow up to 12 days prior to any systemic injection Animals were fed exclusively on a special rodent diet (Tekland 2018S; Harlan Laboratories, Inc.) to reduce autofluorescence.

Ex vivo brain images were obtained with the Maestro In vivo Imaging System (Cambridge Research and Instrumentation, Inc., Woburn, Mass.), and tomographical fluorescent images were acquired using the VisEn Translational Fluorescence In vivo Imaging System, the FMT 2500 (VisEn Medical, Inc., Bedford, Mass.). FMT 2500 analysis began by calibrating the system to the specific fluorescent profile of Pc 4 by imaging a known concentration and volume of Pc 4 in VisEn's calibration probe to correlate intensity of fluorescence with actual concentration of Pc 4 (in pmol). Mice with tumors were anaesthetized with isoflurane and injected intravenously via the tail with either EGF-Au NP-Pc 4 or Au NP-Pc 4 conjugates at a dosage of 1 mg kg$^{-1}$ of Pc 4 per total mouse body weight.

Results

Figure 8:
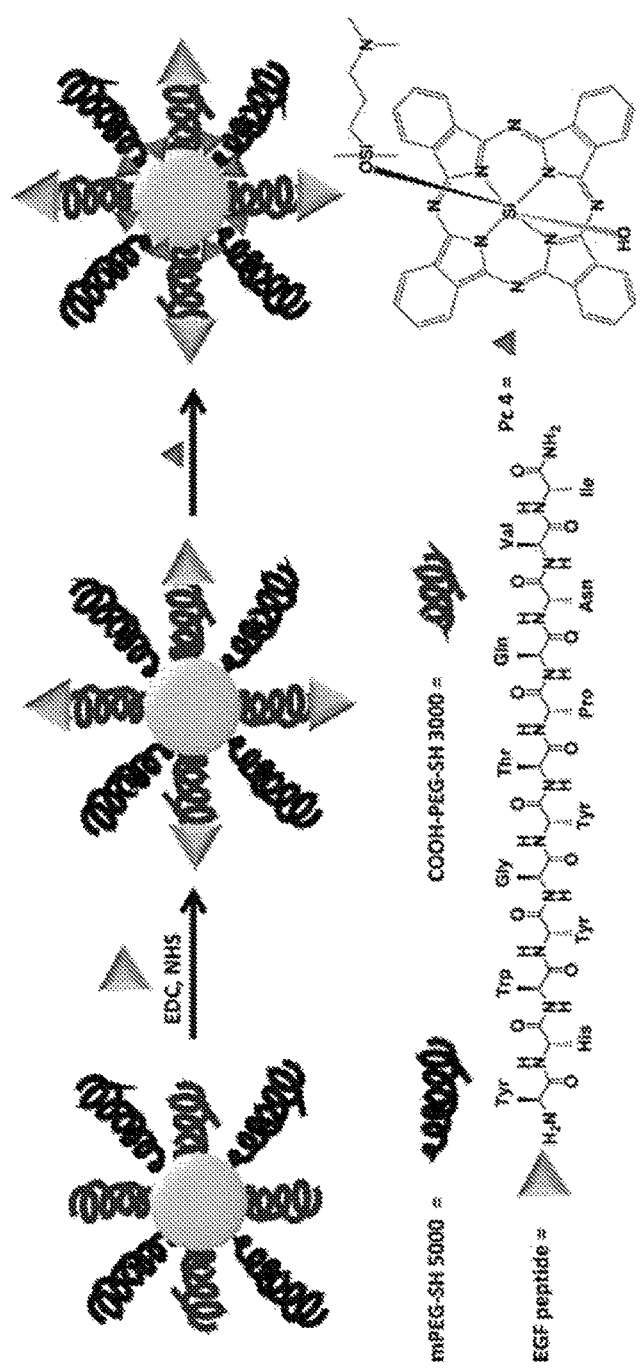
FIG. 8 is a schematic illustration of the design of targeted nanoparticle conjugates that include the PDT drug Pc 4 conjugated to EGF-conjugated Au NP.
Figure 9A:
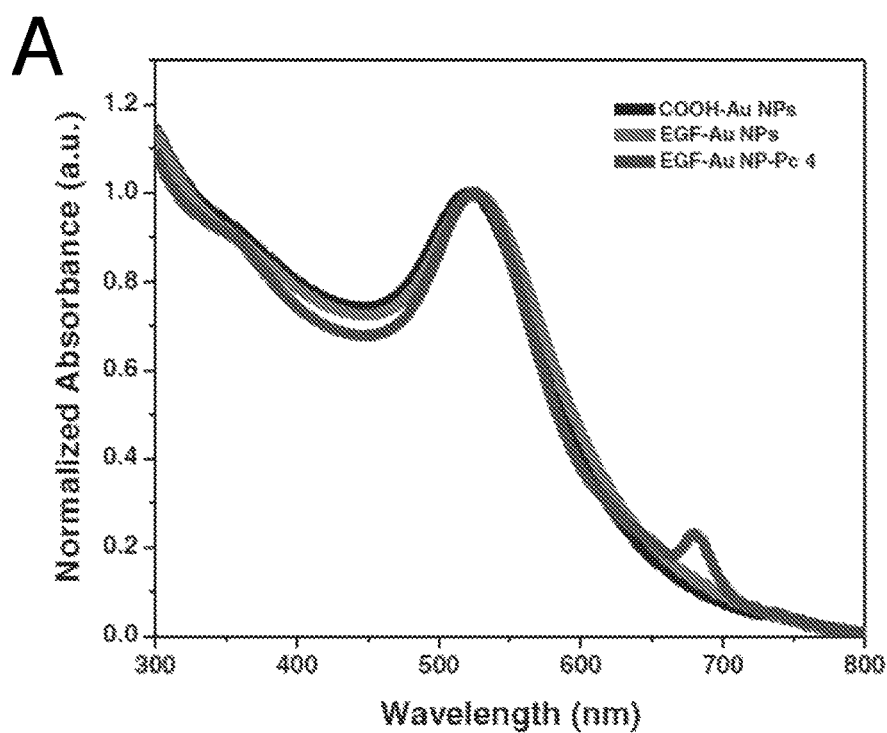
FIG. 9 illustrates: (A) a plot showing absorbance spectra of COOH-functionalized Au NPs, EGF-Au NPs and EGF-Au NP-Pc 4 conjugates in water; (B) a plot showing the fluorescence spectrum of EGF-Au NP-Pc 4 conjugate; (C) an image of 1% agarose gel at 120 V for 4 h in TAE (tris acetate EDTA) buffer of COOH-functionalized Au NP, EGF-Au NPs and EGF-Au NP-Pc 4 conjugates; and (D) a TEM image of the conjugates.
Figure 9B:
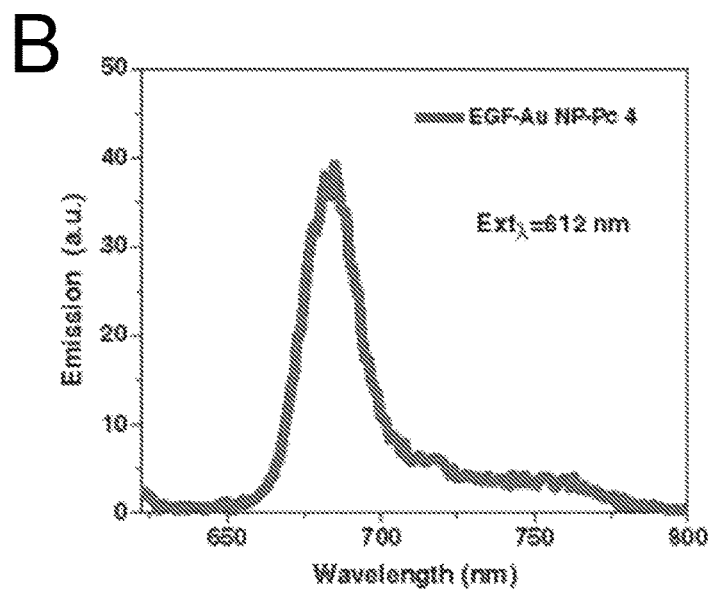
Figure 9C:
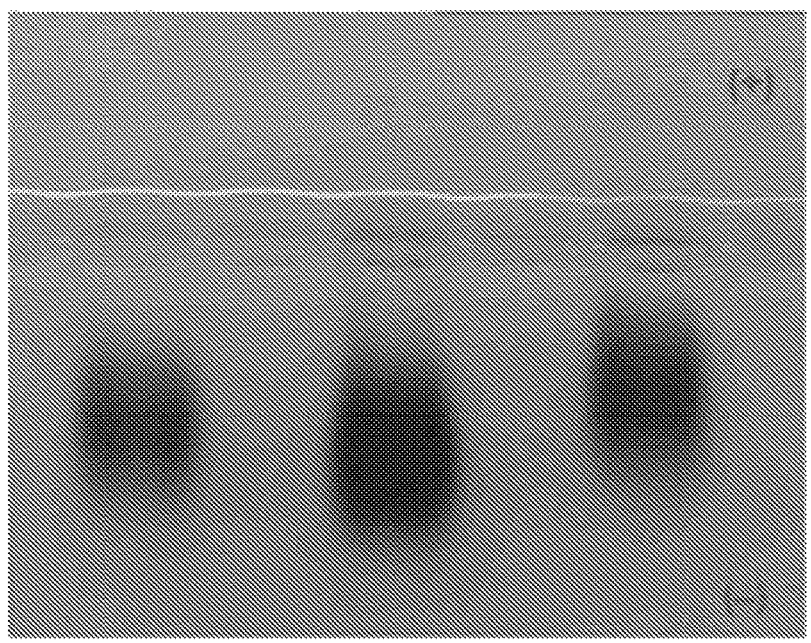
Figure 9D:
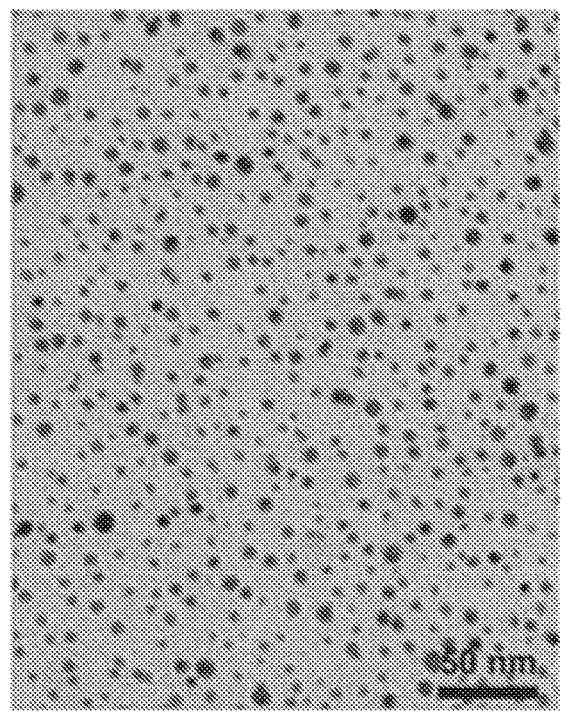

FIG. 8 shows the design of the EGF-Au NP-phthalocyanine (Pc) 4 conjugates.

Without chemical modification of phthalocyanine 4 (Pc 4), a hydrophobic PDT drug currently in clinical trials, the active drug is spatially encaged and photophysically quenched through adsorption onto the PEGylated Au NPs while being transported to the target tissue. The PEG ligand on the Au NPs creates excellent water miscibility, biocompatibility, and long circulation in the blood of the conjugate system. PEG also prevents protein agglomeration on the NP surface. More importantly, the PEG layer provides bifunctionality to conjugate EGF peptides, which are internalizing and nonmitogenic, to recognize EGFRs on the glioma cancer cell surface. The core of Au NPs is designed to be 5 nm in diameter, which is large enough on which to load drug molecules but small enough to be eventually excreted by renal clearance.

PEGylated Au NPs were synthesized and modified with a mixture of 20% heterobifunctional COOH-PEG-SH (MW 3000) and 80% monofunctional mPEG-SH (MW 5000). The EGF peptide with the 12 amino acid sequence YHWYGYT-PQNVI-amide was linked to the carboxyl group on bifunctional PEG layer via the amide bond. Au NPs with the surface plasmon resonance band at 522 nm were well dispersed and stable in aqueous solution before and after conjugation as shown in FIG. 9.

Pc 4 is then adsorbed onto the Au NP surface through N—Au bonding by the terminal amine group on the Pc 4 axial ligand. Since PEG does not contain any unconjugated reactive groups to facilitate this amine attachment, it is likely that the Pc 4 is adsorbed to the surface of the Au NP. This adsorption occurs as a result of both hydrophobic and electrostatic interactions in the PEG corona, close to the gold surface. Synthesis and characterization of the particles is described by Cheng et al. Pc 4 absorption measurements at 679 nm in the UV-vis spectra (FIG. 9) determined that 30±3 Pc 4 molecules were adsorbed per Au NP. The conjugates showed emission at 685 nm due to the intrinsic fluorescence property of Pc 4, which allows detection of drug accumulation via in vitro and in vivo fluorescence imaging. According to TEM analysis (FIG. 9D), the average size of the Au NP core was about 5 nm in diameter. The hydrodynamic diameter of the EGF-Au NP-Pc 4 conjugates was measured to be 42±2 nm by dynamic light scattering (DLS). The EGF-Au NP-Pc 4 conjugates were found to be effectively neutral as indicated by zeta-potential measurements. Gel electrophoresis studies demonstrated clear changes between the COOH-functionalized Au NP, EGF-Au NPs and the conjugates (FIG. 9) indicating successful conjugation. Typically, the samples moved toward the negative electrode in an agarose gel electrophoresis experiment. This is mainly due to electro-osmosis under the applied electric field, which we have recently quantified.

FIG. 10 shows that the PDT drug on the Au NPs is inactive and no toxicity could be detected without irradiation. The activity of Pc 4 on the Au NPs is quenched as measured by photodecomposition of 1,3-diphenylisobenzofuran (DPBF), a commonly used singlet oxygen trap. However, after Pc 4 releases from the Au NPs, the drug activity can be recovered. It can be excited by using near infrared light to transfer the absorbed energy to molecular oxygen and to generate reactive oxygen species such as singlet oxygen to damage surrounding tissues. The dark toxicity and phototoxicity of the EGF-Au NP-Pc 4 conjugates were evaluated with MTT [3-(4,5-Dimethylthiazol-2-yl)-2,5-diphenyltetrazolium bromide; an agent used to calculate viability of cells by assessing mitochondrial reductase activity] assays and trypan blue staining (FIG. 10C). No toxicity was observed upon incubation with the conjugates in the dark. Upon light exposure, the EGF-Au NP-Pc 4 conjugates showed excellent cytotoxicity. Over 90% of cancer cells were killed with 0.5 or 1 J cm$^{-2}$ light exposure at 1 μm drug concentration. Also, a PDT effect of the conjugates could be obtained at half the initial drug concentration, although 30% of the cancer cells survived upon 1 J cm$^{-2}$ light exposure at this lower concentration.

Figure 11A:
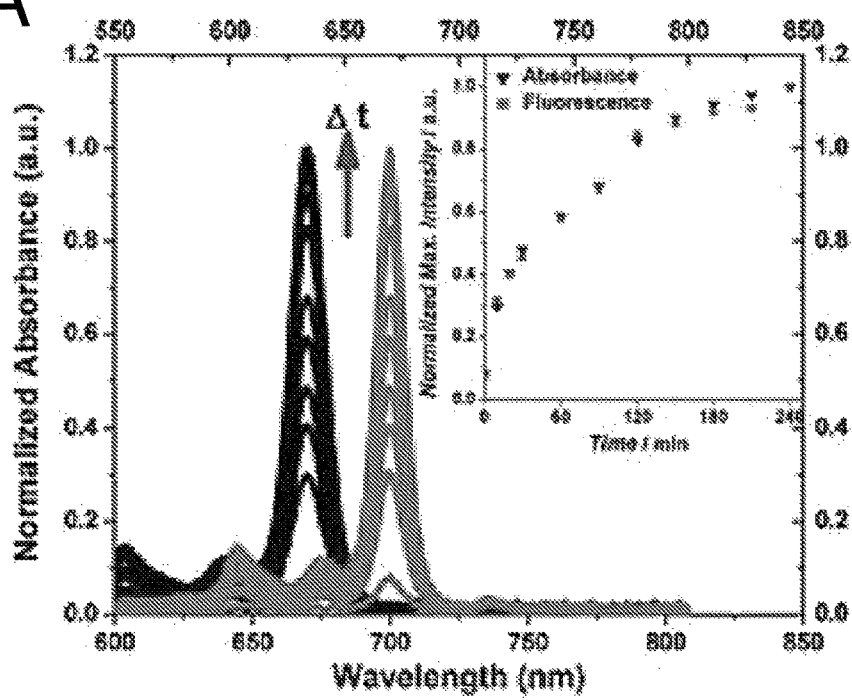
FIG. 11 illustrates: (A) a plot of time dependent drug release in the water-toluene system for in vitro studies of the PDT drug release from EGF-Au NPs; (B) a confocal image of live glioma cancer cells after 4 h incubation with the conjugates; and (C) confocal fluorescence images of fixed glioma cells after incubation for 24 h with EGF-Au NP-Pc 4, [Pc 4]=1 µM.
Figure 11B:
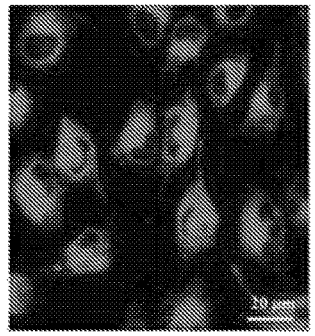

Due to the noncovalent attachment, efficient drug release of the EGF-Au NP-Pc 4 conjugate was found in vitro (FIG. 11). As shown in previous studies, Pc 4 localized in hydrophobic sites such as the lipid bilayers of mitochondria in cells. The water-toluene two-phase system provides a simplified model to study the drug release and transfer from the aqueous phase into a less polar environment. Significant drug release into the organic phase was detected within 4 h as shown in (FIG. 11A), driven by the hydrophobic interaction between the drug and water. The hydrophobic drug was delivered into the toluene rapidly with a time constant of 78±15 min. Similar to the phase transfer studies, the efficient drug uptake into the glioma cancer cells was also observed within 4 h of incubation with the conjugates, as observed by confocal microscopy (FIG. 11B). Pc 4 fluorescence was observed mainly in the cytoplasm and vesicles of the cancer cells.

Figure 11C:
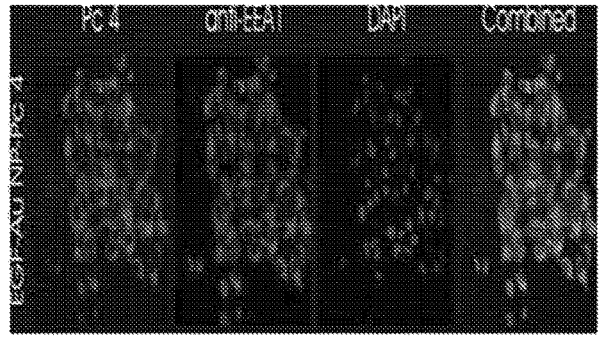

The free EGF peptide has a specific binding to the EGFR with a dissociation constant of 22 nm. After targeting the Au NPs with the EGF peptide, we found that receptor-mediated endocytosis was the dominant pathway and the drug was taken up into the glioma cancer cells through endocytosis with virtually no uptake of the NPs. The conjugate uptake mechanism was studied by TEM, graphite furnace atomic absorption spectroscopy (GFAAS), UV-vis spectrometry, epifluorescence microscopy, and confocal fluorescence microscopy. In contrast to free Pc 4, which is known to locate in the mitochondria, the EGFR-targeted Au NP-Pc 4 conjugates altered the drug-delivery pathway to early endosomes in the glioma cells (FIG. 11C).

TEM imaging showed little Au NP uptake into the cells, in agreement with previous reports of PEGylated Au NP drug-delivery systems. In addition, few NPs were found attached or adjacent to the plasma membrane of the cells. The amount of Au NPs in the cancer cells was also quantified by GFAAS, which confirmed the very low uptake of EGF-Au NPs by the cells at 4 and 24 h after incubation with increased NP uptake after 24 h incubation. The amount of Pc 4 in EGFR-targeted Au NP cells was quantified by UV-vis spectroscopy. Despite the relatively low uptake of Au NPs, as demonstrated by TEM and GFAAS, we found that the Au NPs had different pharmacokinetics as compared to Pc 4. The Pc 4 to Au NP ratio in the cells was $(13.8\pm1.0)\times10^3$:1 after 4 h incubation and $(7.3\pm1.9)\times10^3$:1 after 24 h incubation times. To confirm this drug uptake mechanism, the cells were pre-incubated with free EGF peptide, effectively blocking the receptor-mediated pathway. Fluorescence signal from Pc 4 in the cells decreased in comparison to the control without peptide blocking, demonstrating that the drug release takes place when the EGF-Au NP-Pc 4 conjugates interact with the EGF receptors on the cell surface.

Animal studies showed that the EGF-Au NP-Pc 4 could pass through the BBB/BBTB and targeted drug delivery to the brain tumor (FIG. 12). The drug biodistribution was monitored via its fluorescence. Human glioma cells were implanted and grown in the right hemisphere of the brain of mice. Four hours after intravenous injection with either the EGF-Au NP-Pc 4 or untargeted Au NP-Pc 4 conjugates, the mice were euthanized and sacrificed, as reported previously. The brains were removed and then serially transected. In contrast to the untargeted Au NPs, a striking accumulation of the drug in the brain tumor was observed in the EGFR-targeted conjugate injected mice as shown in the fluorescence images of the serial transections in FIG. 12. A 10-fold increase of the drug accumulated in the tumor as quantified by fluorescence molecular tomography compared to that of the untargeted ones. The EGF peptide-modified conjugates therefore pass through the BBB/BBTB efficiently and transport the drug into the brain. It should also be noted that the conjugates were small enough to leak through the BBTB, which restricts the total Au NP size to 100 nm or less, and selectively accumulated in the tumor region by additional EPR effect and receptor-mediated endocytosis. Only tumor regions showed increased Pc 4 fluorescence with extremely low Pc 4 accumulation in the healthy brain tissue (FIG. 12). Biodistribution studies have demonstrated that most tissues, including the tumor, reached maximum Au NP accumulation by 4 h followed by a gradual decrease over time. An exception to this was observed in the spleen where accumulation of the Au NPs continued over time to reach a maximum at the latest time point measured, 7 days, where liver and spleen together showed a maximum Au NP accumulation of 20% of the injected dose. Gold content was found in the urine samples which indicated the excretion of Au NPs through renal clearance.

In conclusion, we demonstrate that EGFR targeting of Pc 4-loaded Au NPs to the cell surface receptor significantly improves their capacity to deliver drug cargo into brain tumors. These results are interesting and novel in two respects. First, our data suggest that increased drug delivery occurs with significant increases in the uptake of Pc 4 by targeted tissues. The increase in drug delivery occurs via a novel mechanism. Very few Au NPs can be found within targeted cells suggesting that the EGF-peptide receptor interaction likely allows for a prolonged interaction of the particles at the cell surfaces, allowing the hydrophobic Pc 4 to transfer to the cellular membrane. Untargeted Au NPs were 10-fold less effective at delivering the drug to cells in vivo. Second, when conjugated to EGFR-targeted Au NPs, therapeutic levels can be realized within 4 h after administration and the drug is internalized through early endosomal compartments. These studies demonstrate the rational and successful design of a noncovalent drug-delivery system to brain tumors using targeted Au NPs.

From the above description of the application, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

Having described the invention, the following is claimed:

1. A composition for treating a disorder in a subject, the composition comprising:
   a polyethylene glycolylated (PEGylated) nanoparticle;
   at least one hydrophobic therapeutic agent non-covalently coupled to the surface of the nanoparticle, wherein the at least one hydrophobic therapeutic agent has an amino or amine functionality for attachment to the surface of the nanoparticle; and
   at least one targeting moiety coupled to polyethylene glycol of the nanoparticle for targeting the composition to a cell associated with the disorder, wherein the at least one therapeutic agent is released from the nanoparticle and differentially up taken by the cell upon targeting with reduced nanoparticle accumulation in the cell.

2. The composition of claim 1, wherein the disorder is cancer and the at least one targeting moiety targets the composition to a cancer cell.

3. The composition of claim 2, wherein the at least one hydrophobic therapeutic agent is an anti-cancer agent.

4. The composition of claim 3, wherein the anti-cancer agent comprises Phthalocyanine 4.

5. The composition of claim 2, wherein the at least one targeting moiety comprises a polypeptide that binds to epidermal growth factor receptor (EGFR).

6. The composition of claim 5, wherein the polypeptide comprises an epidermal growth factor (EGF) peptide having the amino acid sequence of SEQ ID NO: 1.

7. A composition for treating cancer in a subject, the composition comprising:
   a polyethylene glycolylated (PEGylated) gold nanoparticle;
   at least one hydrophobic anti-cancer agent non-covalently coupled to the surface of the gold nanoparticle, wherein the at least one hydrophobic anti-cancer agent has an amino or amine functionality for attachment to the surface of the nanoparticle; and
   at least one targeting moiety coupled to polyethylene glycol of the nanoparticle for targeting the composition to a cancer cell, wherein the at least one anti-cancer agent is released from the nanoparticle and differentially up taken by a cancer cell upon targeting with reduced nanoparticle accumulation in the cell.

8. The composition of claim 7, wherein the at least one anti-cancer agent comprises Phthalocyanine 4.

9. The composition of claim 7, wherein the at least one targeting moiety comprises a polypeptide that binds to epidermal growth factor receptor (EGFR).

10. The composition of claim 9, wherein the polypeptide comprises an epidermal growth factor (EGF) peptide having the amino acid sequence of SEQ ID NO: 1.

11. A composition for treating brain cancer, the composition comprising:
    a polyethylene glycolylated (PEGylated) gold nanoparticle;
    Phthalocyanine 4 non-covalently conjugated to the PEGylated gold nanoparticle; and
    a polypeptide coupled to polyethylene glycol of the nanoparticle, the polypeptide binding epidermal growth factor receptor (EGFR), wherein the Phthalocyanine 4 is released from the nanoparticle and differentially up taken by brain cancer cells upon targeting with reduced nanoparticle accumulation in the cell.

12. The composition of claim 11, wherein the polypeptide consists of the amino acid sequence of SEQ ID NO: 1.

13. The composition of claim 11, wherein the composition upon systemic administration to the subject crosses the blood brain barrier and targets the brain cancer cells.

14. The composition of claim 13, wherein the Phthalocyanine 4 upon uptake is activated by light to cause the cancer death or suppress the cancer growth.

15. The composition of claim 1, wherein the at least one hydrophobic therapeutic agent is selected from the group consisting of Phthalocyanine 4, 5-aminolevulinic acid, rosiglitazone, and pioglitazone.

16. The composition of claim 7, wherein the at least one hydrophobic anti-cancer agent is selected from the group consisting of Phthalocyanine 4, 5-aminolevulinic acid, rosiglitazone, and pioglitazone.

* * * * *